US008221804B2

(12) United States Patent
Stock et al.

(10) Patent No.: US 8,221,804 B2
(45) Date of Patent: Jul. 17, 2012

(54) COMPOSITIONS AND METHODS FOR ENHANCING COGNITIVE FUNCTION

(75) Inventors: Jeffry B. Stock, Rocky Hill, NJ (US); Maxwell Stock, Rocky Hill, NJ (US); Haoming Gu, Plainsboro, NJ (US); Gregory B Stock, Princeton, NJ (US); Zhu Li, Princeton, NJ (US); Peter Michael Wolanin, Princeton, NJ (US)

(73) Assignees: Signum Biosciences, Inc., Princeton, NJ (US); Trustees of Princeton University, Princeton, NJ (US)

( * ) Notice: Subject to any disclaimer, the term of this patent is extended or adjusted under 35 U.S.C. 154(b) by 1063 days.

(21) Appl. No.: 11/346,706

(22) Filed: Feb. 3, 2006

(65) Prior Publication Data

US 2006/0171938 A1    Aug. 3, 2006

Related U.S. Application Data

(60) Provisional application No. 60/649,902, filed on Feb. 3, 2005.

(51) Int. Cl.
*A61K 36/258* (2006.01)
*A61K 36/82* (2006.01)
*A61K 36/81* (2006.01)
*A61K 36/16* (2006.01)
*A61K 36/87* (2006.01)

(52) U.S. Cl. ........ 424/728; 424/729; 424/730; 424/751; 424/752; 424/754; 424/766; 424/725

(58) Field of Classification Search .................. None
See application file for complete search history.

(56) References Cited

U.S. PATENT DOCUMENTS

| | | | |
|---|---|---|---|
| 2,852,520 A | 9/1958 | Robinson | |
| 3,832,253 A | 8/1974 | Di Palma et al. | |
| 3,854,480 A | 12/1974 | Zaffaroni | |
| 4,105,027 A | 8/1978 | Lundquist | |
| 4,185,118 A | 1/1980 | Kathawala | |
| 4,192,309 A | 3/1980 | Poulsen | |
| 4,194,002 A | 3/1980 | Kathawala | |
| 4,201,785 A | 5/1980 | Kathawala | |
| 4,227,522 A | 10/1980 | Carris | |
| 4,229,463 A | 10/1980 | Kathawala | |
| 4,248,893 A | 2/1981 | Kathawala et al. | |
| 4,409,253 A | 10/1983 | Morrison, Jr. et al. | |
| 4,448,785 A | 5/1984 | Kathawala et al. | |
| 4,452,775 A | 6/1984 | Kent | |
| 4,627,432 A | 12/1986 | Newell et al. | |
| 4,658,063 A | 4/1987 | Tahara et al. | |
| 4,667,014 A | 5/1987 | Nestor, Jr. et al. | |
| 4,709,094 A | 11/1987 | Weber et al. | |
| 4,748,034 A | 5/1988 | de Rham | |
| 4,811,731 A | 3/1989 | Newell et al. | |
| 4,900,749 A | 2/1990 | Matsumoto et al. | |
| 4,906,779 A | 3/1990 | Weber et al. | |
| 4,933,324 A | 6/1990 | Shashoua | |
| 4,935,422 A | 6/1990 | Patil et al. | |
| 4,939,174 A | 7/1990 | Shashoua | |
| 4,977,170 A | 12/1990 | Matsumoto et al. | |
| 5,035,237 A | 7/1991 | Newell et al. | |
| 5,075,109 A | 12/1991 | Tice et al. | |
| 5,093,525 A | 3/1992 | Weber et al. | |
| 5,175,183 A | 12/1992 | Brooks et al. | |
| 5,189,049 A | 2/1993 | Frehel et al. | |
| 5,190,976 A | 3/1993 | Weber et al. | |
| 5,239,660 A | 8/1993 | Ooi | |
| 5,284,876 A | 2/1994 | Shashoua et al. | |
| 5,322,858 A | 6/1994 | Canfield et al. | |
| 5,502,056 A | 3/1996 | Breitbarth | |
| 5,527,811 A | 6/1996 | Natsugari et al. | |
| 5,565,491 A | 10/1996 | Schieven | |
| 5,585,358 A | 12/1996 | Bialer et al. | |
| 5,585,513 A | 12/1996 | Matthews et al. | |
| 5,668,180 A | 9/1997 | Lesieur et al. | |
| 5,670,499 A | 9/1997 | Cho et al. | |
| 5,684,033 A | 11/1997 | Cho et al. | |
| 5,693,627 A | 12/1997 | Schieven | |
| 5,700,821 A | 12/1997 | Lazo et al. | |
| 5,714,094 A | 2/1998 | Bertholet et al. | |
| 5,777,162 A | 7/1998 | Matthews et al. | |
| 5,795,877 A | 8/1998 | Jackson et al. | |

(Continued)

FOREIGN PATENT DOCUMENTS

AU          64586       12/1994

(Continued)

OTHER PUBLICATIONS

Abolhassani et al., "Hyperosmolarity Causes Inflammation through the Methylation of Protein Phosphatase 2A," Inflammation Research, 2008, 57(9), pp. 419-429, ISSN: 1023-3830.

Acker et al., "Photometric determination of shell constituents in cocoa products," 1966, *Suesswaren* (Hamburg), 15(10):622-4, 626-8.

Aggen et al., "The Design, Synthesis, and Biological Evaluation of Analogues of the Serine-threonine Protein Phosphatase 1 and 2A Selective Inhibitor Microcystin LA: Rational Modifications Imparting PP1 Selectivity," Bioorganic & Medicinal Chemistry, 1999, 7(3), pp. 543-564, ISSN: 0968-0896.

Albaugh et al., "Determination of distance distribution from time domain fluorometry," 1989, *J of Physical Chemistry*, 93(24):8013-16.

Alonso et al., "Alzheimer's disease hyperphosphorylated tau sequesters normal tau into tangles of filaments and disassemles microtubules," 1996, *Nat Med*, 2(7):783-787.

(Continued)

*Primary Examiner* — Christopher R Tate
*Assistant Examiner* — Randall Winston
(74) *Attorney, Agent, or Firm* — Beverly W. Lubit; Greenberg Traurig, LLP

(57) ABSTRACT

The invention encompasses novel compositions containing a methylation modifying compound isolated from botanical raw materials, including a fruit of the genus *Coffea*, and microbial raw materials, methods of making such compositions, and methods of treating or preventing human disease using such compositions. The methylation modifying compound in botanical extracts of the present invention can dramatically increase the level of methylation of PP2A, thus increasing cognitive function, particularly in persons suffering from or prone to developing Alzheimer's disease.

27 Claims, 7 Drawing Sheets

U.S. PATENT DOCUMENTS

| | | |
|---|---|---|
| 5,821,261 A | 10/1998 | Durette et al. |
| 5,824,662 A | 10/1998 | Slusher et al. |
| 5,849,764 A | 12/1998 | Goulet et al. |
| 5,856,506 A | 1/1999 | Lazo et al. |
| 5,863,536 A | 1/1999 | Jackson et al. |
| 5,880,132 A | 3/1999 | Hill |
| 5,902,817 A | 5/1999 | Jackson et al. |
| 5,914,242 A | 6/1999 | Honkanen et al. |
| 5,925,660 A | 7/1999 | Lazo et al. |
| 5,939,563 A | 8/1999 | Matthews |
| 5,962,521 A | 10/1999 | Jackson et al. |
| 5,977,090 A | 11/1999 | Slusher et al. |
| 5,981,526 A | 11/1999 | Hargreaves |
| 5,985,855 A | 11/1999 | Slusher et al. |
| 5,994,392 A | 11/1999 | Shashoua |
| 6,004,946 A | 12/1999 | Slusher et al. |
| 6,013,658 A | 1/2000 | Lau et al. |
| 6,017,903 A | 1/2000 | Slusher et al. |
| 6,025,344 A | 2/2000 | Jackson et al. |
| 6,040,323 A | 3/2000 | Lazo et al. |
| 6,046,180 A | 4/2000 | Jackson et al. |
| 6,048,868 A | 4/2000 | Fourtillan et al. |
| 6,054,444 A | 4/2000 | Jackson et al. |
| 6,071,965 A | 6/2000 | Jackson et al. |
| 6,107,499 A | 8/2000 | Shashoua |
| 6,129,918 A * | 10/2000 | Amagase ............... 424/754 |
| 6,132,973 A | 10/2000 | Lal et al. |
| 6,140,324 A | 10/2000 | Tattersall |
| 6,159,704 A | 12/2000 | Hemmings |
| 6,180,624 B1 | 1/2001 | Hill |
| 6,200,768 B1 | 3/2001 | Mandelkow et al. |
| 6,232,110 B1 | 5/2001 | Pallas et al. |
| 6,271,245 B1 | 8/2001 | Jackson et al. |
| 6,277,566 B1 | 8/2001 | Beachy et al. |
| 6,288,046 B1 | 9/2001 | Jackson et al. |
| 6,300,363 B1 | 10/2001 | Stevens et al. |
| 6,303,610 B1 | 10/2001 | Johnson et al. |
| 6,306,912 B1 | 10/2001 | Mueller et al. |
| 6,337,344 B1 | 1/2002 | Defossa et al. |
| 6,350,767 B1 | 2/2002 | Lau et al. |
| 6,353,015 B1 | 3/2002 | Oxenkrug et al. |
| 6,372,752 B1 | 4/2002 | Staveski et al. |
| 6,376,205 B1 | 4/2002 | Wischik et al. |
| 6,399,796 B2 | 6/2002 | Schwartz |
| 6,403,577 B1 | 6/2002 | Cho et al. |
| 6,451,468 B1 | 9/2002 | Adachi |
| 6,458,392 B1 | 10/2002 | Okawa et al. |
| 6,462,086 B1 | 10/2002 | Kloog et al. |
| 6,465,457 B1 | 10/2002 | Matthews et al. |
| 6,492,128 B1 | 12/2002 | Haklai et al. |
| 6,503,949 B1 | 1/2003 | Lau et al. |
| 6,528,295 B2 | 3/2003 | Pallas et al. |
| 6,528,655 B1 | 3/2003 | N'Zemba et al. |
| 6,541,468 B1 | 4/2003 | Roder et al. |
| 6,551,816 B1 | 4/2003 | Bontoux et al. |
| 6,562,807 B2 | 5/2003 | Jorgensen et al. |
| 6,608,196 B2 | 8/2003 | Wang et al. |
| 6,653,304 B2 | 11/2003 | Leftheris et al. |
| 6,669,979 B1 | 12/2003 | Zhao et al. |
| 6,683,055 B1 | 1/2004 | Hillen et al. |
| 6,727,255 B1 | 4/2004 | Cho et al. |
| 6,750,359 B1 | 6/2004 | Copeland et al. |
| 6,760,359 B2 | 7/2004 | Evans |
| 6,818,655 B2 | 11/2004 | Dhanak et al. |
| 6,852,734 B2 | 2/2005 | Yamamoto et al. |
| 6,869,957 B1 | 3/2005 | Cho et al. |
| 6,869,975 B2 | 3/2005 | Abe et al. |
| 6,875,760 B2 | 4/2005 | Lau et al. |
| 6,921,527 B2 | 7/2005 | Platz et al. |
| 6,946,485 B2 | 9/2005 | Kloog et al. |
| 6,953,812 B2 | 10/2005 | Jorgensen et al. |
| 7,019,008 B2 | 3/2006 | Dhanak et al. |
| 7,041,702 B1 | 5/2006 | Durant et al. |
| 7,115,634 B2 | 10/2006 | Thurieau et al. |
| 7,157,456 B2 | 1/2007 | Straub et al. |
| 7,166,637 B2 | 1/2007 | Hofgen et al. |
| 7,173,027 B2 | 2/2007 | Makriyannis et al. |
| 7,241,923 B2 | 7/2007 | Fagerhad et al. |
| 7,282,593 B2 | 10/2007 | Nair et al. |
| 7,358,248 B2 | 4/2008 | Whitehouse et al. |
| 7,393,861 B2 | 7/2008 | Thurieau et al. |
| 7,459,472 B2 | 12/2008 | Mjalli et al. |
| 7,476,399 B2 | 1/2009 | Tachdjian et al. |
| 2001/0044459 A1 | 11/2001 | Jackson et al. |
| 2001/0056116 A1 | 12/2001 | Shashoua |
| 2002/0034524 A1 | 3/2002 | Poret |
| 2002/0107374 A1 | 8/2002 | Pallas et al. |
| 2002/0119972 A1 | 8/2002 | Leftheris et al. |
| 2002/0143186 A1 | 10/2002 | Jorgensen et al. |
| 2002/0160067 A1 | 10/2002 | Zapp et al. |
| 2003/0013846 A1 | 1/2003 | Wang et al. |
| 2003/0036070 A1 | 2/2003 | Chakravarti |
| 2003/0050226 A1 | 3/2003 | Shashoua |
| 2003/0100750 A1 | 5/2003 | Wang et al. |
| 2003/0149108 A1 | 8/2003 | Abe et al. |
| 2003/0153610 A1 | 8/2003 | Straub et al. |
| 2003/0171411 A1 | 9/2003 | Kodra et al. |
| 2003/0186416 A1 | 10/2003 | Pallas et al. |
| 2003/0215456 A1 | 11/2003 | Yao et al. |
| 2003/0220350 A1 | 11/2003 | Lau et al. |
| 2004/0006089 A1 | 1/2004 | Thurieau et al. |
| 2004/0022822 A1 | 2/2004 | Poret |
| 2004/0024045 A1 | 2/2004 | Jorgensen et al. |
| 2004/0053963 A1 | 3/2004 | Dhanak et al. |
| 2004/0058963 A1 | 3/2004 | Yamamoto et al. |
| 2004/0063757 A1 | 4/2004 | Dhanak et al. |
| 2004/0077851 A1 | 4/2004 | Makriyannis et al. |
| 2004/0096547 A1 | 5/2004 | Ferruzzi |
| 2004/0138224 A1 | 7/2004 | Dhanak et al. |
| 2004/0138238 A1 | 7/2004 | Dhanoa et al. |
| 2004/0147759 A1 | 7/2004 | Hofgen et al. |
| 2004/0152692 A1 | 8/2004 | Dhanak et al. |
| 2004/0176444 A1 | 9/2004 | Fagerhad et al. |
| 2004/0209934 A1 | 10/2004 | McCluskey et al. |
| 2004/0242655 A1 | 12/2004 | Anziano |
| 2004/0253356 A1 | 12/2004 | Fields |
| 2004/0266789 A1 | 12/2004 | Whitehouse et al. |
| 2004/0266822 A1 | 12/2004 | Wang et al. |
| 2005/0031761 A1 * | 2/2005 | Brucker et al. ............... 426/595 |
| 2005/0043292 A1 | 2/2005 | Parker et al. |
| 2005/0043388 A1 | 2/2005 | Bombrun et al. |
| 2005/0049310 A1 | 3/2005 | Mjalli et al. |
| 2005/0059713 A1 | 3/2005 | Mjalli et al. |
| 2005/0059727 A1 | 3/2005 | Nair et al. |
| 2005/0074831 A1 | 4/2005 | Jerecic et al. |
| 2005/0084506 A1 | 4/2005 | Tachdjian et al. |
| 2005/0129827 A1 | 6/2005 | Miljkovic et al. |
| 2005/0181041 A1 | 8/2005 | Goldman |
| 2005/0197345 A1 | 9/2005 | Dhanak et al. |
| 2005/0203108 A1 | 9/2005 | Lau et al. |
| 2005/0239796 A1 | 10/2005 | Thurieau et al. |
| 2005/0245547 A1 | 11/2005 | Kim et al. |
| 2005/0250819 A1 | 11/2005 | Li et al. |
| 2005/0250839 A1 | 11/2005 | Marnett et al. |
| 2005/0261197 A1 | 11/2005 | Aoki |
| 2005/0261332 A1 | 11/2005 | Distefano et al. |
| 2006/0045953 A1 | 3/2006 | Tachdjian et al. |
| 2006/0063789 A1 | 3/2006 | Freyne et al. |
| 2006/0159773 A1 * | 7/2006 | Holt ............... 424/646 |
| 2006/0160109 A1 | 7/2006 | MacDonald et al. |
| 2006/0171938 A1 | 8/2006 | Stock et al. |
| 2006/0178378 A1 | 8/2006 | Dai et al. |
| 2006/0199806 A1 | 9/2006 | Failli et al. |
| 2006/0223842 A1 | 10/2006 | Moriconi et al. |
| 2006/0258724 A1 | 11/2006 | Straub et al. |
| 2006/0270741 A1 | 11/2006 | Durant et al. |
| 2006/0293362 A1 | 12/2006 | Norbert et al. |
| 2007/0031909 A1 | 2/2007 | Stock et al. |
| 2007/0082907 A1 | 4/2007 | Canada et al. |
| 2007/0088072 A1 | 4/2007 | Di Marzo et al. |
| 2007/0093531 A1 | 4/2007 | Hofgen et al. |
| 2007/0105940 A1 | 5/2007 | Di Marzo et al. |
| 2007/0129424 A1 | 6/2007 | Di Marzo et al. |
| 2007/0149514 A1 | 6/2007 | Woltering et al. |
| 2007/0161644 A1 | 7/2007 | Stockwell |
| 2007/0191357 A1 | 8/2007 | Antel et al. |
| 2007/0197629 A1 | 8/2007 | Somei et al. |

| | | | |
|---|---|---|---|
| 2007/0203209 A1 | 8/2007 | Bartolini et al. | |
| 2007/0212677 A1 | 9/2007 | MacDonald et al. | |
| 2007/0225283 A1 | 9/2007 | Hammock et al. | |
| 2007/0238775 A1 | 10/2007 | Ruah et al. | |
| 2007/0243134 A1 | 10/2007 | Makriyannis et al. | |
| 2007/0259945 A1 | 11/2007 | De Petrocellis et al. | |
| 2007/0280918 A1 | 12/2007 | Schwartz et al. | |
| 2008/0021198 A1 | 1/2008 | Shi et al. | |
| 2008/0027099 A1 | 1/2008 | Govek et al. | |
| 2008/0027112 A1 | 1/2008 | Govek et al. | |
| 2008/0039442 A1 | 2/2008 | Blom et al. | |
| 2008/0090815 A1 | 4/2008 | Straub et al. | |
| 2008/0161341 A1 | 7/2008 | Calderwood et al. | |
| 2008/0161351 A1 | 7/2008 | Abe et al. | |
| 2008/0176846 A1 | 7/2008 | Chianelli et al. | |
| 2008/0176854 A1 | 7/2008 | Quintana-Ruiz | |
| 2008/0200473 A1 | 8/2008 | Falco et al. | |
| 2008/0200674 A1 | 8/2008 | Straub et al. | |
| 2008/0213406 A1 | 9/2008 | Stock et al. | |
| 2008/0221197 A1 | 9/2008 | Lam et al. | |
| 2008/0287516 A1 | 11/2008 | Wu et al. | |
| 2009/0005430 A1 | 1/2009 | Somei et al. | |
| 2009/0029355 A1* | 1/2009 | Zhao et al. | 435/6 |

FOREIGN PATENT DOCUMENTS

| | | |
|---|---|---|
| AU | 690107 | 12/1994 |
| AU | 2006230674 | 11/2006 |
| CA | 2125236 | 12/1994 |
| CN | 1205175 | 1/1999 |
| CN | 1304396 | 7/2001 |
| CN | 1403137 A | 3/2003 |
| CN | 1415596 | 5/2003 |
| CN | 1687072 | 10/2005 |
| DE | 3105850 | 8/1982 |
| EP | 0693547 A1 | 1/1996 |
| EP | 714968 | 6/1996 |
| FR | 1238756 A | 8/1960 |
| FR | 2827866 A1 | 1/2003 |
| FR | 2879601 | 6/2006 |
| JP | 3268073 | 11/1991 |
| JP | 4156825 | 5/1992 |
| JP | 06025276 | 2/1994 |
| JP | 07052542 | 2/1995 |
| JP | 3795093 | 6/1996 |
| JP | 08151366 | 6/1996 |
| JP | 09301954 | 11/1997 |
| JP | 10077229 | 3/1998 |
| JP | 10077267 | 3/1998 |
| JP | 2000037188 A | 2/2000 |
| JP | 2001247539 | 9/2001 |
| JP | 2002193923 | 7/2002 |
| JP | 2002255837 A | 9/2002 |
| JP | 2003137780 | 5/2003 |
| JP | 2004292383 | 10/2004 |
| JP | 2007145763 | 6/2007 |
| JP | 2008207466 | 9/2008 |
| JP | 2009001564 | 1/2009 |
| KR | 2003038383 | 10/2002 |
| KR | 2003088329 | 11/2003 |
| SU | 357508 | 1/1973 |
| WO | WO-9116038 A1 | 10/1991 |
| WO | WO-9206955 | 4/1992 |
| WO | WO-9222559 | 12/1992 |
| WO | WO-9707117 | 2/1997 |
| WO | WO-9806695 | 2/1998 |
| WO | WO-9901103 | 1/1999 |
| WO | WO-9901118 A2 | 1/1999 |
| WO | WO-9945926 | 9/1999 |
| WO | WO-0116334 A2 | 3/2001 |
| WO | WO-0120995 | 3/2001 |
| WO | WO-0121606 | 3/2001 |
| WO | WO-0157535 A2 | 8/2001 |
| WO | WO-0241700 A1 | 5/2002 |
| WO | WO-02060462 A2 | 8/2002 |
| WO | WO-02085397 A1 | 10/2002 |
| WO | WO-02102397 A1 | 12/2002 |
| WO | WO-03008632 | 1/2003 |
| WO | WO-03078448 A1 | 9/2003 |
| WO | WO-2004002504 A1 | 1/2004 |
| WO | WO-2004031177 | 4/2004 |
| WO | WO-2004063147 | 7/2004 |
| WO | WO-2005009349 A2 | 2/2005 |
| WO | WO-2005037839 | 4/2005 |
| WO | WO-2005071101 | 8/2005 |
| WO | WO-2005084664 A1 | 9/2005 |
| WO | WO-2005089502 | 9/2005 |
| WO | WO-2006015258 A2 | 2/2006 |
| WO | WO-2006028226 | 3/2006 |
| WO | WO-2006084033 A1 | 8/2006 |
| WO | WO-2006094235 | 9/2006 |
| WO | WO-2006101456 | 9/2006 |
| WO | WO-2006104826 | 10/2006 |
| WO | WO-2006117549 A1 | 11/2006 |
| WO | WO-2007008514 | 1/2007 |
| WO | WO-2007015866 | 2/2007 |
| WO | WO-2007079930 | 7/2007 |
| WO | WO-2007140551 | 12/2007 |
| WO | WO-2008007123 | 1/2008 |
| WO | WO-2008019357 | 2/2008 |
| WO | WO-2008031509 | 3/2008 |
| WO | WO-2008060791 A2 | 5/2008 |
| WO | WO-2008061781 | 5/2008 |
| WO | WO-2008110196 | 9/2008 |
| WO | WO-2008112525 | 9/2008 |
| WO | WO-2008113760 | 9/2008 |
| WO | WO-2008127387 A2 | 10/2008 |
| WO | WO-2008141013 | 11/2008 |
| WO | WO-2008155666 | 12/2008 |
| WO | WO-2008155668 | 12/2008 |
| WO | WO-2009020596 | 2/2009 |

OTHER PUBLICATIONS

Alonso et al., "Hyperphosphorylation induces self-assembly of T into tangles of paired helical filaments / straight filaments," 2001, *Proc Natl Acad Sci U S A*, 98:6923-2928.

Alonso et al., "Protein Tyrosine Phosphatases in the Human Genome," 2004, *Cell*, 117:699-711.

Alonso et al., "Role of abnormally phosphorylated tau in the breakdown of microtubules in Alzheimer disease," 1994, *Proc Natl Acad Sci U S A*, 91:5562-5566.

Appendino et al., "First 'hybrid' ligands of vanilloid TRPV1 and cannabinoid CB2 receptors and non-polyunsaturated fatty acid-derived CB2-selective ligands," 2006, *FEBS Letters*, 580(2):568-574.

Arino et al., "Human liver phosphatase 2A: cDNA and amino acid sequence of two catalytic subunit isotypes," 1988, *Proc Nat'l. Acad Sci. USA*, 85:4252-4256.

Ascherio et al., "Prospective Study of Caffeine Consumption and Risk of Parkinson's Disease in Men and Women," 2001, *Ann Neurol*, 50:56-63.

Bai et al., "Huperzine A, A Potential therapeutic Agent for Treatment of Alzheimer's Disease," 2000, *Current Medicinal Chemistry*, 7:355-374.

Battini et al., "Determination of N-Alkanoyl-5-Hydroxytryptamines (C-5-HT) in Coffee Beans by Means of HPLC and TLC," Annali di Chimica, 1989, 79(7-8), pp. 369-377.

Baumann, et al., "Abnormal Alzheimer-like phosphorylation of tau-protein by cyclin-dependent kinases cdk2 and cdk5," 1993, *FEBS*, 336(3):417-424.

Bialy et al., "Synthesis and Biological Evaluation of Cytostatin Analogues," Chemical Communications, 2003, 15, pp. 1872-1873, ISSN: 1359-7345.

Bialy et al., "Synthesis of the Protein Phosphatase 2A Inhibitor (4S,5S,6S,10S,11S,12S)—cytostatin," Angewandte Chemie, International Edition, 2002, 41(10), pp. 1748-1751, ISSN: 1433-7851.

Biernat et al., "Phosphorylation of Ser$^{262}$ Strongly Reduces Binding of Tau to Microtubules: Distinction between PHF-like Immunoreactivity and Microtubule Binding," 1993, *Neuron*,11:153-163.

Billingsley et al., "Regulated phosphorylation and dephosphorylation of tau protein: effects on microtubule interaction, intracellular trafficking and neurodegeneration," 1997, *Biochem J.*, 323:577-91.

Blickenstaff et al., "Potential radioprotective agents-V. Melatonin analogs. Oral activity of p-aminopropiophenone and its ethylene ketal," 1994, *Bioorganic & Medicinal Chemistry* 2(10):1057-60.

Blickenstaff et al., "Potential radioprotective agents. 1. Homologs of melatonin," 1994, *J. of Pharmaceutical Sciences*, 83(2):216-18.

Blickenstaff et al., "Potential radioprotective agents. VI. Chalcones, benzophenones, acid hydrazides, nitro amines and chloro compounds. Radioprotection of murine intestinal stem cells," 1995, *Bioorganic & Medicinal Chemistry* 3(7):917-22.

Boger et al., "Total Synthesis of Fostriecin (CI-920)," Journal of the American Chemical Society, 2001, 123(18), pp. 4161-4167, ISSN: 0002-7863.

Borsotto et al., "PP2A-Bγ subunit and KCNQ2K$^+$ channels in bipolar disorder," 2007, *Pharmacogenomics J.*, 7:123-132.

Boushey et al., "A quantitative assessment of plasma homocysteine as a risk factor for vascular disease," 1995, *Jama*, 274:1049-1057.

Bramblett, et al, "Abnormal Tau Phosphorylation at Ser$^{396}$ in alzheimer's Disease Receapitulates Development and Contributes to Reduced Microtubule Binding," 1993, *Neuron*, 10:1089-1099.

Breitner, John, "Inflammatory Processes and Antinflammatory Drugs in Alzheimer's Disease: A Current Appraisal," 1996, *Neurobiology of Aging*, 17(5):789-794.

Brookmeyer et al., "Forecasting the global burden of Alzheimer disease," 2007, *Alzheimer's and Dementia*, 3(3):186-191.

Bryant et al., "Methylated C-terminal Leucine Residue of PP2A Catalytic Subunit is Important for Binding of Regulatory Bα Subunit," Biochemical Journal, 1999, 339(2), pp. 241-246, ISSN: 0264-6021.

Buznikov et al., "5-Hydroxytryptamides and 3-hydroxytyramides of polyenoic fatty acids as a tool for studying the pre-nervous biogenic monoamines' functions," 2000, *Rossiiskii Fiziologicheskii Zhumal imeni I. M. Sechenova*, 86(9):1093-1108 (English language abstract in Appendix A).

Buée et al., "Tau protein isoforms, phosphorylation and role in neurodegenerative disorders," 2000, *Brain Res. Rev.*, 33(1):95-130.

Caudill et al., "Intracellular S-Adenosylhomocysteine Concentrations Predict Gobal DNA Hypomethylation in Tissues of Methyl-Deficient Cystathionine β-Synthase Heterozygous Mice," 2001, *American Society for Nutritional Sciences*, 131:2811-2818.

Cavin et al., "Cafestol and kahweol, two coffee specific diterpenes with anticarcinogenic activity," 2002, *Food and Chemical Toxicology*, 40:1155-1163.

Ceulemans et al., "Functional Diversity of Protein Phosphatase-1, a Cellular Economizer and Reset Button," 2004, *Physiol. Rev.*, 84:1-39.

Chan et al., "Folate Deprivation Increases Tau Phosphorylation by Homocysteine-induced Calcium Influx and by Inhibition of Phosphatase Activity: Alleviation by S-adenosyl Methionine," Brain Research, 2008, 1199, pp. 133-137, ISSN: 0006-8993.

Chandra et al., "Incidence Alzheimer's disease ina rural community in India," 2001, *Neurology*, 57(6).

Chao et al., "Structure and Mechanism of the Phosphotyrosyl Phosphatase Activator," 2006, *Molecular Cell*, 23(4):535-546.

Chavez et al., "Tryptamine Derived Amides and Acetogenins from the Seeds of *Rollinia mucosa*," 1999, *J. of Natural Products*, 62(8):1119-1122.

Chen et al., "Cheritamine, a new N-fatty acyl tryptamine and other consituents from the stems of *Annona cherimola*," 1999, *J. of the Chinese Chemical Society* (Taipei), 46(1):77-86.

Chen et al., "Comparison of Protein Phosphatase Inhibition Activities and Mouse Toxicities of Microcystins," Toxicon, 2006, 47(7), pp. 742-746, ISSN: 0041-0101.

Chen et al., "Improved Synthesis and Characterization of L-histidine Norcantharimide, a Novel Potent Protein Phosphatase 2A Inhibitor," Journal of Chinese Pharmaceutical Sciences, 2008, 17(2), pp. 134-137, ISSN: 1003-1057.

Chen et al., "Lithium Inhibits Ceramide- and Etoposide-induced Protein Phosphatase 2A Methylation, Bcl-2 Dephosphorylation, Caspase-2 Activation, and Apoptosis," Molecular Pharmacology, 2006, 70(2), pp. 510-517, ISSN: 0026-985X.

Chiang et al., "S-Adenosylmethionine and methylation," 1996, *Faseb J*, 10:471-80.

Cho & Xu, "Crystal Structure of a Protein Phosphatase 2A Heterotrimeric Holoenzyme," 2007, *Nature*, 445:53-57.

Christen et al., "Inhibition of Alpha Interferon Signaling by Hepatitis B Virus," Journal of Virology, 2007, 81(1), pp. 159-165, ISSN: 0022-538X.

Clarke et al., "Folate, Vitamin B$_{12}$, and Serum Total Homocysteine Levels in Confirmed Alzheimer Disease," 1998, *Arch Neurol*, 55:1449-1155.

Clarke et al., "Hyper homocysteinemia: an independent risk factor for vascular disease," 1991, *N Engl J Med*, 324:1149-1155.

Cohen et al., "Protein Phosphatases Come of Age," 1989, *J. Biol. Chem.*, 264(36):21435-21438.

Cohen et al., "Protein serine/threonine phosphatases; an expanding family," 1990, *FEBS*, 268(2):355-359.

Da Baere et al., "Purification of Porcine Brain Protein Phosphatase 2A Leucine Carboxyl Methyltransferase and Cloning of the Human Homologue," Biochemistry, 1999, 38(50), pp. 16539-16547, ISSN: 0006-2960.

Delgado-Reyes et al., "Immunohistochemical Detection of Betaine-Homocysteine S-Methyltransferase in Human, Pig, and Rat Liver and Kidney," 2001, *Arch Biochem Biophys*, 393(1):184-186.

Deshmukh et al., "Acute Modulation of PP2A and Troponin I Phosphorylation in Ventricular Myocytes: Studies with a Novel PP2A Peptide Inhibitor," American Journal of Physiology, 2007, 292(2, Pt. 2), pp. H792-H799, ISSN: 0002-9513.

Deventer et al., "Lower Esophageal Sphincter Pressure, Acid Secretion, and Blood Gastrin after Coffee Consumption," 1992, *Digestive Diseases and Sciences*, 37(4):558-569.

Du, "5mI2 Mediated Aryl Radical Cyclization/Sequential Anionic Capture on Solid Support and Computational Studies on Hapalosin and its Analogs and on Inhibitors of Protein Phosphatases PP1 and PP2A," University of California, Los Angeles, 1998, 142 pp. Avail.: UMI, Order No. DA9818006, From: Diss. Abstract Int., B 1998, 58(12), pp. 6581.

Dumanchin et al., "Segregation of a missense mutation in the microtubule-associated protein tau gene with familial frontotemporal dementia and parkinsonism," 1998, *Hum. Mol. Genet.*, 7:1825-1829.

Duong et al., "Hepatitis C Virus Inhibits Interferon Signaling through Up-regulation of Protein Phosphatase 2A," Gastroenterology, 2004, 126(1), pp. 263-277, ISSN: 0016-5085.

Duong et al., "S-adenosylmethionine and Betaine Correct Hepatitis C Virus Induced Inhibition of Interferon Signaling in Vitro," Hepatology, 2006, 43(4), pp. 796-806, ISSN: 02709139.

Duong et al., "Upregulation of Protein Phosphatase 2Ac by Hepatitics C Virus Modulates NS3 Helicase Activity throught Inhibition of Protein Arginine Methyltransferase 1," Journal of Virology, 2005, 79(24), pp. 15342-15350, ISSN: 0022-538X.

Duval et al., "analogues of cytotoxics squamocin using reliable reactions: new insights into the reativity and role of the α,β-unsaturated lactone of the annonaceous acetogenins," 2006, *Tetrahedron*, 62(26):6248-6257.

European Search Opnion, Communication regarding the transmission of the European Search Report, and Supplementary European Search Report for EP 1843734, Aug. 7, 2008.

Evans et al., "Functional Expression of Human PP2Ac in Yeast Permits the Identification of Novel C-terminal and Dominant-negative Mutant Forms," Journal of Biological Chemistry, 1999, 274(34), pp. 24038-24046, ISSN: 0021-9258.

Evans et al., "Mutation of the C-terminal Leucine Residue of PP2Ac Inhibits PR55/B Subunit Binding and Confers Supersensitivity to Microtubule Destabilization in Saccharomyces cerevisiae," Molecular and General Genetics, 2000, pp. 264(4), pp. 425-432, ISSN: 0026-8925.

Favre et al., "Differential Inhibition and Posttranslational Modification of Protein Phosphatase 1 and 2A in MCF7 Cells Treated with Calyculin-A, Okadaic Acid, and Tautomycin," Journal of Biological Chemistry, 1997, 272(21), pp. 13856-13863, ISSN: 0021-9258.

Favre et al., "The Catalytic Subunit of Protein Phosphatase 2A is Carboxyl-Methylated in Vivo," Journal of Biological Chemistry, 1994, 269(23), pp. 16311-16317, ISSN: 0021-9258.

Finkelstein J.D., "The metabolism of homocysteine: pathways and regultion," 1998, *Eur J Pediatr*, 157(Suppl 2):540-4.

Floer et al., "Carboxyl Methylation of Protein Phosphatase 2A from *Xenopus* Eggs is Stimulated by cAMP and Inhibited by Okadaic Acid," Biochemical and Biophysical Research Communications, 1994, 198(1), pp. 372-379, ISSN: 0006-291X.

Folstar et al., "Liquid chromatographic coffee wax analysis," 1977, *Colloque Scientifique International sure le Café*, 8:121-124.

Folstar et al., "Liquid Chromatographie Analysis of N-b)-Alkanoyl-5-Hydroxytryptamine (C-F-Ht) in Green Coffee Beans," Journal of Agricultural and Food Chemistry, 1979, 27(1), pp. 12-15.

Folstar et al., "New tryptamine derivatives isolated from wax of green coffee beans", J. Agric. Food Chem., 1980, vol. 28(4), pp. 872-874.

Fowler et al., "Inhibition of Fatty Acid Amidohydrolase, the Enzyme Responsible for the Metabolism of the Endocannabinoid Anandamide, by Analogues of Arachidonoyl-serotonin," 2003, *J. of Enzyme Inhibition and Medicinal Chemistry*, 18(3):225-231.

Fujita, E., "A new efficient aminolysis and its application to synthesis of macrolactam alkaloids," 1981, *Pure and Applied Chemistry*, 53(6):1141-54.

Gentry et al., "A Novel Assay for Protein Phosphatase 2A (PP2A) Complexes in Vivo Reveals Differential Effects of Covalent Modifications on Different *Saccharomyces cerevisiae* PP2A Heterotrimers," Eukaryotic Cell, 2005, 4(6), pp. 1029-1040, ISSN: 1535-9778.

George et al., "Chaperonin Assisted Overexpression, Purification, and Characterisation of Human PP2A Methyltransferase," Protein Expression and Purification, 2002, 26(2), pp. 266-274, ISSN: 1046-5928.

Gibbons et al., "Expression of Human Protein Phosphatase-1 in *Saccharomyces cerevisiae* Highlights the Role of Phsphatase Isoforms in Regulating Eukaryotic Functions," 2007, *J. Biol. Chem.*, 282(30):21838-21847.

Goedert et al., "p42 map kinase phophorylation sites in microtubule-associated protein tau are dephosphorylated by protein phosphatase 2A," 1992, *FEBS*, 312(1):95-99.

Goedert et al., "Reduced Binding of protein Phsphatase 2A to Tau Protein with Frontotemporal Dementia and Parkinsonism Linked to Chromosome 17 Mutations," 2000, *J. Neurochem*, 75:2155-2162.

Goldstein et al., "Microtubule-Bases Transport Systems in Nurons: the Roles of Kinesins and Dyneins," 2000, *Annu Rev Neurosci*, 23:39-71.

Gong et al., "Phosphatase activity toward abnormally phosphorylated tau: decrease in Alzheimer disease brain," 1995, *J. Neurochem.*, 65:732-738.

Gonzalez et al., "Total Synthesis of Thyrsiferyl 23-Acetate, a Specific Inhibitor of Protein Phosphatase 2A and an Anti-Leukemic Inducer of Apoptosis," Journal of the American Chemical Society, 2000, 122(38), pp. 9099-9108, ISSN: 0002-7863.

Gotz, J. et al., "Formation of Neurofibrillary Tangles in P30 1L Tau Transgenic Mice Induced by Aβ42 Fibrils," 2001, *Science*, 293:1491-1495.

Gozzo et al., "Structure-activity relationships in a series of melatonin analogues with the low-density lipoprotein oxidation model," 1999, *Free Radical Biology & Medicine*, 22(11/12):1538-1543.

Green et al., "Molecular cloning and sequence analysis of the catalytic subunit of bovine type a protein phosphatase," 1987, *Proc Nat'l Acad. Sci USA*, 84:4880-4884.

Greenberg et al., "Hydrofluoric Acid-treated T $_{PHF}$ Proteins Display the Same biochemical Properties as Normal T*," 1992, *J. Biol. Chem.*, 267(1):564-569.

Guenin et al., "PP2A Activity is Controlled by Methylation and Regulates Oncoprotein Expression in Melanoma Cells: A Mechanism which Participates in Growth Inhibition Induced by Chloroethylnitrosourea Treatment," International Journal of Oncology, 2008, 32(1), pp. 49-57, ISSN: 1019-6439.

Guergnon et al., "Use of Penetrating Interacting with PP1/PP2A Proteins as a General Approach for a Drug Phosphatase Technology," 2006, *Mol. Pharmacol.*, 69(4):1115-1124.

Gulledge et al., "Linearized and Truncated Microcystin Analogues as Inhibitors of Protein Phosphatases 1 and 2A," Bioorganic & Medicinal Chemistry Letters, 2003, 13(17), pp. 2903-2906, ISSN: 0960-840X.

Gulledge et al., "Microcystin Analogues Comprised Only of Adda and a Single Additional Amino Acid Retain Moderate Activity as PP1/PP2A Inhibitors," Bioorganic & Medicinal Chemistry Letters, 2003, 13(17), pp. 2907-2911, ISSN: 0960-894X.

Guo et al., "ATM-dependent Dissociation of B55 Regulatory Subunit from Nuclear PP2A in Response to Ionizing Radiation," Journal of Biological Chemistry, 2002, 277(7), pp. 4839-4844, ISSN: 0021-9258.

Hahn et al., "Synthesis of 1-alkylisoquinolines and 1,1'-polymethylenediisoquinolines," 1938, *Berichte der Deutschen Chemischen Gesellschaft [Abteilung] B: Abhandlungen*, 71B:2183-91.

Hahn et al., "Synthesis of 3-alkyl-4-carbolines and 3,3'-polymethylenedi-4-carbolines," 1938, *Berichte der Deutschen Chemischen Gesellschaft [Abteilung] B: Abhandlungen*, 71B:2175-82.

Harms et al., "Carboxylic Acid 5-Hydroxytryptamides in Coffee Beans," Zeitschrift fuer Lebensmittel-Untersuchung und-Forschung, 1968, 138(2), pp. 75-80. (English Abstract provided).

Harms et al., "Carboxylic Acid 5-Hydroxytryptamides in Coffee Beans," Zeitschrift fuer Lebensmittel-Untersuchung und-Forschung, 1968, 138(2), pp. 75-80. (English Abstract provided). (English Language).

Hart et al., "Modified Norcantharidins Synthesis, Protein Phosphatases 1 and 2A Inhibition, and Anticancer Activity," Bioorganic & Medicinal Chemistry Letters, 2004, 14(8), pp. 1969-1973, ISSN: 0960-894X.

Hemmings et al., "α and β Forms of 65-kDA Subunit of Protein Phosphatase 2A Have a Similar 39 Amino Acid Repeating Structure," 1990, *Biochemistry*, 29:3166-3173.

Hendrix et al., "Analysis of Subunit Isoforms in Protein Phosphatase 2A Holoenzymes from Rabbit *Xenopus*," 1993, *J. biol. Chem.*, 268:7330-7337.

Hill et al, "Heterocyclic Substituted Cantharidin and Norcantharidin Analogues-synthesis, Protein Phosphatase (1 and 2A) Inhibition, and Anti-cancer Activity," Bioorganic & Medicinal Chemistry Letters, 2007, 17(12), pp. 3392-3397, ISSN: 0960-894X.

Hombauer et al., "Generation of Active Protein Phosphatase 2A is Coupled to Holoenzyme Assembly," PLoS Biology, 2007, 5(6), pp. 1355-1365, ISSN: 1545-7885.

Hornstein et al., "Protein Phosphatase and TRAIL Receptor Genes as New Candidate Tumor Genes on Chromosome 8p in Prostate Cancer," Cancer Genomics & Proteomics, 2008, 5(2), pp. 123-136, ISSN: 1109-6535.

Huang et al., "Molecular Cloning, Expression, and Characterization of a Novel Human Serine/Threonine protein Phosphatase, PP7, that is Homologous to *Drosophila* Retinal Degeneration C Gene Product (rdgC)*," 1998, *J. Biol. Chem.*, 273(3):1462-1468.

Hubert et al., "Analysis of Carboxylic Acid Hydroxytryptamides in Coffee," Fresenius' Zeitschrift fuer Analytische Chemie, 1977, 285(3), pp. 242-250.

Hug et al., "Development of a Gas-Liquid Chromatographic Method for the Analysis of Fatty Acid Tryptamides in Cocoa Products," 2006, *J of Agricultural and Food Chemistry*, 54(9):3199-3203.

Hunter et al., "Protein Kinases and Phosphatases: The Ying and Yang of Protein Phosphorylation and Signaling," 1995, *Cell*, 80:225-236.

Hunziker et al., "High-pressure Liquid Chromatographie Determination of 5-Hydroxytryptamide in Coffee," Mitteilungen aus dem Gebiete der Lebensmitteluntersuchung und Hygiene, 1979, 70(1), pp. 142-152. (English Abstract provided).

Hunziker et al., "High-pressure Liquid Chromatographie Determination of 5-Hydroxytryptamide in Coffee," Mitteilungen aus dem Gebiete der Lebensmitteluntersuchung und Hygiene, 1979, 70(1), pp. 142-152. (English Abstract provided). (English Language).

Hunziker, "Determination of 5-Hydroxytryptamide in Coffee Using High-Pressure Liquid Chromatography," Mitteilungen aus dem Gebiete der Lebensmitteluntersuchung und Hygiene, 1977, 68(2), pp. 267-274. (English Abstract provided).

Hunziker, "Determination of 5-Hydroxytryptamide in Coffee Using High-Pressure Liquid Chromatography," Mitteilungen aus dem Gebiete der Lebensmitteluntersuchung und Hygiene, 1977, 68(2), pp. 267-274. (English Abstract provided). (English Language).

Hutton et al., "Association of missense and 5'-splice site mutations in tau with the inherited dentia FTDP-17," 1998, *Nature*, 393:702-705.

Ikehara et al., "Baculovirus Expression, Purification, and Characterization of Human Protein Phosphatase 2A Catalytic Subunits α and β ," Protein Expression and Purification, 2006, 45(1), pp. 150-156, ISSN: 1046-5928.

Ikehara et al., "Methylation of the C-terminal Leucine Residue of the PP2A Catalytic Subunit is Unncecessary for the Catalytic Activity and the Binding of Regulatory Subunit (PR55/B)," Biochemical and Biophysical Research Communications, 2007, 354(4), pp. 1052-1057, ISSN: 0006-291X.

International Search Report for PCT/US2003/07658, Aug. 11, 2003.
International Search Report for PCT/US2006/03686, Jun. 15, 2006.
International Search Report for PCT/US2007/81260, Sep. 11, 2008.
International Search Report for PCT/US2007/82833, Oct. 9, 2008.
International Search Report for PCT/US2009/41321, Jun. 1, 2009.

Jackson-Lewis et al., "Protocol for the Mptp mouse model of Parkinson's disease," 2007, Nature Protocols, 2(1):141-152.

Janssen et al., "Fatty Acid Tryptamides as shell indicators for cocoa products and as quality parameters for cocoa butter," 2002, European Food Research and Technology, 214(3):259-264.

Janssens et al., "PP2A: the expected tumor suppressor," 2005, Curr Opin. Genet. Dev., 15:34-41.

Janssens et al., "Protein Phosphatase 2A: A Highly Regulated Family of Serine/Threonine Phosphatases Implicated in Cell Growth and Signaling," Biochemical Journal, 2001, 353(3), pp. 417-439, ISSN: 0264-6021.

Jayaprakasam et al., "Potent lipid peroxidation inhibitors from withania somnifera fruits," 2004, Tetrahedron 60(13):3109-3121.

Jiang et al., "The effects of aging on gene expression in the hypothalamus and cortex of mice," 2001, Proc Natl Acad Sci U S A. 98(4):1930-1934.

Jicha et al., "Alz-50 and MC-1, a New Monoclonal Antibody Raised to Paired Helical Filaments, Recognize Conformational Epitopes on Recombinant Tau," 1997, J. Neurosci Res., 48(2):128-132.

Kalhor et al., "Protein Phosphatase Methyltransferase 1 (Ppm1p) is the Sole Activity Responsible for Modification of the Major Forms of Protein Phosphatase 2A in Yeast," Archives of Biochemistry and Biophysics, 2001, 395(2), pp. 239-245, ISSN: 0003-9861.

Kamibayashi, C. et al., J. Biol. Chem. 269 (31): 20139.

Keen et al., "Epigenetic Regulation of Protein Phosphatase 2A (PP2A), Lymphotactin (XCL1) and Estrogen Receptor Alpha (ER) Expression in Human Breast Cancer Cells," Cancer Biology & Therapy, 2004, 3(12), pp. 1304-1312, ISSN: 1538-4047.

Kele et al., Determination of serotonin released from coffee wax by liquid chromatography, 1996, J. of Chromatography, 730:59-62.

Khew-Goodall et al., "Tissue-specific expression of mRNAs encoding α and β catalytic subunits of protein phosphatase 2A," 1988, FEBS Lett, 238:265-268.

Khil et al., "Hydrogen Peroxide Mediates Brazilin-induced Glucose Transport in Adipocytes," Journal of Applied Pharmacology, 2004, 12(4), pp. 228-234, ISSN: 1225-6110.

Kins et al., "Reduced Poteing Phosphatase 2A Activity Induces Hyperphosphorylation and Altered Compartmentalization of Tau in Transgenic Mice," 2001, J Biol Chem, 276:38193-200.

Kita et al., "Structure-activity Relationship of Okadaic Acid, a Potent Protein Phosphatases PP1 and PP2A Inhibitor: 24-Epi-Okadaic Acid and a 18-membered Lactone Analog," Heterocycles, 2008, 76(2), pp. 1033-1042, ISSN: 0385-5414.

Kloeker et al., "Carboxymethylation of Nuclear Protein Serine/Threonine Phosphatase X," Biochemical Journal, 1997, 327(2), pp. 481-486, ISSN: 0264-6021.

Kobayashi et al., "Process Formation of Podocytes: Morphogenetic Activity of Microtubules and Regulation by Protein Serine/Threonine Phosphatase PP2A," Histochemistry and Cell Biology, 2001, 115(3), pp. 255-266, ISSN: 0948-6143.

Koenig et al., "Gas Chromatography and Mass Spectrometry as Aids in Studying High-Boiling Coffee Compounds," Institut fur Organische Chemie und Biochemie, pp. 271-278; and Colloque Scientifique International sur le Cafe (1983), vol. Date 1982, 10th. (English Abstract provided).

Koenig et al., "Gas Chromatography and Mass Spectrometry as Aids in Studying High-Boiling Coffee Compounds," Institut fur Organische Chemie und Biochemie, pp. 271-278; and Colloque Scientifique International sur le Cafe (1983), vol. Date 1982, 10th. (English Abstract provided). (English Language).

Konoki et al., "Direct Observation of Binding Between Biotinylated Okadaic Acids and Protein Phosphatase 2A Monitored by Surface Plasmon Resonance," Tetrahedron Letters, 1999, 40(5), pp. 887-890, ISSN: 0040-4039.

Koren et al., "The Scaffolding A/Tpd3 Subunit and High Phosphatase Activity are Dispensable for Cdc55 Function in the Saccharomyces cerevisiae Spindle Checkpoint and in Cytokinesis," Journal of Biological Chemistry, 2004, 279(47), pp. 48598-48606, ISSN: 0021-9258.

Kowluru et al., "Carboxylmethylation of the Catalytic Subunit of Protein Phosphatase 2A in Insulin-secreting Cells: Evidence for Functional Consequences on Enzyme Activity and Insulin Secretion," Endocrinology, 1996, 137(6), pp. 2315-2323, ISSN: 0013-7227.

Kowluru et al., "Ceramide-activated Protein Phosphatase-2A Activity in Insulin-secreting Cells," FEBS Letters, 1997, 418(1, 2), pp. 179-182, ISSN: 0014-5793.

Kowluru et al., "Purine Nucleotide- and Sugar Phosphate-induced Inhibition of the Carboxyl Methylation and Catalysis of Protein Phosphatase-2A in Insulin-secreting Cells: Protection by Divalent Cations," Bioscience Reports, 1998, 18(4), pp. 171-186, ISSN: 0144-8463.

Kowluru, "Bridging the Gap Between Protein Carboxyl Methylation and Phospholipid Methylation to Understand Glucose-stimulated Insulin Secretion from the Pancreatic β Cell," Biochemical Pharmacology, 2008, 75(2), pp. 335-345, ISSN: 0006-2952.

Kraulis, "MOLSCRIPT: a program to produce both detailed and schematic plots of protein structures," 1991, J. Appl. Crystallogr., 24:946-950.

Krebs & Fisher, "Conversion of Phosphorylase β to Phosphorylase a in Muscle Extracts," 1955, J. Biol. Chem., 216:121-132.

Krebs & Fisher, "Phosphorylase Activity of Skeletal Muscle Extracts," 1955, J. Biol. Chem., 216:113-120.

Kurzrock et al., "Chromatography of Carbonic Acid-5-Hydroxyltryptamides," Institute of Food Chemistry, pp. 305-308; and Colloque Scientifique International sur le Cafe (2005), vol. Date 2004, 20th.

Lang et al., "A Versatile Method for the Quantitative Determination of bN-Alkanoy1-5-Hydroxytryptamides in Roasted Coffee," European Food Research and Technology, 2005, 220(5-6), pp. 638-643.

Laub et al., "[ADMAdda5]-microcysins in Planktothrix agardhii Strain PH-123 (Cyanobacteria)—Importance of Monitoring of Microcystins in the Environment," Environmental Toxicology, 2002, 17(4), pp. 351-357, ISSN: 1520-4081.

Lawhorn et al, "Total Synthesis of Cytostatin," Heterocycles, 2006, 70, pp. 65-70, ISSN: 0385-5414.

Lawhorn et al., "Total Synthesis and Evaluation of Cytostatin, Its C10-C11 Diastereomers, and Additional Key Analogues: Impact on PP2A Inhibition," Journal of the American Chemical Society, 2006, 128(51), pp. 16720-16732, ISSN: 0002-7863.

Le Bars et al., "Influence of the Severity of Cognitive Impairment on the Effect of the Ginkgo biloba Extract EGb 761 in alzheimer's Disease," 2002, Neuropsychobiology, 45:19-26.

Lechward et al., "Protein Phosphatase 2A: Variety of Forms and Diversity of Functions," Acta Biochimica Polonica, 2001, 48(4), pp. 921-933, ISSN: 0001-527X.

Lee et al., "A Specific Protein Carboxyl Methylesterase that Demethylates Phosphoprotein Phosphatase 2A in Bovine Brain," Proceedings of the National Academy of Sciences of the United States of America, 1996, 93(12), pp. 6043-6047, ISSN: 0027-8424.

Lee et al., "Leucine Carboxyl Methyltransferase-1 is Necessary for Normal Progression through Mitosis in Mammalian Cells," Journal of Biological Chemistry, 2007, 282(42), pp. 30974-30984, ISSN: 0021-9258.

Lee et al., "Mechanisms of Parkinson's Deseas Linked to Pathological α*Synuclein: New Targets for Drug Discovery," 2006, Neuron, 52:33-38.

Lee et al., "Neurodegenerative Tauopathies," 2001, Annu Rev Neurosci, 24:1121-1159.

Lee et al., "Protein Phosphatase 2A Catalytic Subunit Is Methylesterified at Its Carboxyl Terminus by a Novel Methyltransferase," 1993, *J. Biol. Chem.*, 268(26):19192-19195.

Leulliot et al., "Structure of Protein Phosphatase Methyltransferase 1 (PPM1), a Leucine Carboxyl Methyltransferase Involved in the Regulation of Protein Phosphatase 2A Activity," Journal of Biological Chemistry, 2004, 279(9), pp. 8351-8358, ISSN: 0021-9258.

Lewis et al., "Enhanced Neurofibrillary Degeneration in Transgenic Mice Expressing Mutant Tau and App," 2001, *Science*, 293:1487-1491.

Li et al., "Disruption of microtubule network by Alzheimer abnormally hyperphosphorylated tau," 2007, *Acta Neuropathol.*, 113:501-11.

Li et al., "Okadaic Acid and Microcystin-LR Directly Inhibit the Methylation of Protein Phosphatase 2A by its Specific Methyltransferase," Biochemical and Biophysical Research Communcations, 1994, 202(2), pp. 1023-1030, ISSN: 0006-291X.

Li, Zhu, "Post-Translational Carboxyl Methylation of Protein Phosphatase 2A: a Therapeutic Target," 2008, *Dissertation Presented to Dept. of Chemistry at Princeton University*, 1-175.

Lim et al., "The Curry Spice Curcumin Redues Oxidative Damage and Amyloid Pathology in an Alzheimer Transgenic Mouse," 2001, *J of Neuroscience*, 21(2):8370-8377.

Lindsay et al., "Risk Factors for Alzheimer's Disease: A Prospective Analysis from the Canadian Study of Health and Aging," 2002, *Am. J. Epidemiol.*, 156(5):445-53.

Litvan, Irene, "Update on Epidemiological Aspects of Progressive Supranulear Palsy," 2003, *Movement Disorders*, 18(6):543-550.

Liu et al., "Antiadrenergic Effects of Adenosine Al Receptor-mediated Protein Phosphatase 2a Activation in the Heart," American Journal of Physiology. Heart and Circulatory Physiology. 2002, 283, (4, Pt. 2), H1314-H1321, ISSN: 0002-9513.

Longin et al., "Selection of Protein Phosphatase 2A Regulatory Subunits is Mediated by the C Terminus of the Catalytic Subunit," Journal of Biological Chemistry, 2007, 282(37), pp. 26971-26980, ISSN: 0021-9258.

Lucock, M., "Folic Acid: Nutritional biochemistry, Molecular Biology, and Role in Disease Processes," 2000, *Mol Genet Metab*, 71:121-138.

Maeda et al., "N-Fatty acyl tryptamines from *Annona reticulata*," 1993, *Phytochemistry*, 34(6):1633-5 (English language abstract in Appendix A).

Maki et al., "Catalyst-controlled Asymmetric Synthesis of Fostriecin and 8-epi-Fostriecin," Journal of the American Chemical Society, 2005, 127(48), 17111-17117, ISSN: 0002-7863.

Mancini et al., "Synthesis and Bioactivity of Linear Oligomers Related to Polymeric Alkylpyridinium Metabolites from the Mediterranean Sponge *Reniera sarai*," Organic & Biomolecular Chemistry, 2004, 2(9), pp. 1368-1375, ISSN: 1477-0520.

Manning et al., "The Protein Kinase Complement of the Human Genome," 2002, *Science*, 298:1912-1934.

Mano, M.L., "Silicic acid col. chromatography in the separation of components of food fats," 1965, *Revista Portuguesa de Farmacia*, 15(3):398-401.

Martin De La Vega et al., "Cerebral Postischemic Reperfusion-induced Demethylation of the Protein Phosphatase 2A Catalytic Subunit," Journal of Neuroscience Research, 2002, 69(4), pp. 540-549, ISSN: 0360-4012.

Martin et al., "Identification and determination of peanut oil mixed with permissible edible oils," 1964, *Medicamenta*, 32(16):9-12 (English language abstract in Appendix A).

Marx, J., "Alzheimer disease: A new take on tau," 2007, *Science*, 316(5830):1416-1417.

Maude et al., "Design and Preparation of Serine-Threonine Protein Phosphatase Inhibitors Based Upon the Nodularin and Microcystin Toxin Structures: Part 2. Synthesis of a Functionalized Nodularin Macrocycle and a Stripped-down Microcystin Macrocycle," Journal of the Chemical Society, Perkin Transactions 1: Organic and Bio-Organic Chemistry, 1997, 17, pp. 2513-2526, ISSN: 0300-922X.

Mazanetz et al., "Untangling tau hyperphosphorylation in drug design for neurodegenerative disease," 2007, *Nat. Rev. Drug Discovery*, 6:464-479.

McCaddon et al., "Total Serum Homocysteine in Senile Dementia of Alzheimer Type," 1998, *Int J Geriatr Psychiatry*, 13:235-239.

McCluskey et al., "Anhydride Modified Cantharidin Analogues. Is Ring Opening Important in the Inhibition of Protein Phosphatase 2A?," European Journal of Medicinal Chemistry, 2000, 35(10), pp. 957-964, ISSN: 0223-5234.

McCluskey et al., "Anhydride Modified Cantharidin Analogues: Synthesis, Inhibition of Protein Phosphatases 1 and 2A and Anticancer Activity," Bioorganic & Medicinal Chemistry Letters, 2000, 10(15), pp. 1687-1690, ISSN: 0960-0894X.

McCLUSKEY et al., "The First Two Cantharidin Analogues Displaying PP1 Selectivity," Bioorganic & Medicinal Chemistry Letters, 2002, 12(3), pp. 391-393, ISSN: 0960-894X.

McCluskey et al., "The Inhibition of Protein Phosphatases 1 and 2A: A New Target for Rational Anti-Cancer Drug Design," 2001, *Anti-Cancer Drug Design*, 16:291-303.

Mehrotra et al., "Design and Preparation of Serine-Threonine Protein Phosphatase-inhibitors Based Upon the Nodularin and Microcystin Toxin Structures. Part 1. Evaluation of Key Inhibitory Features and Synthesis of a Rationally Stripped-down Nodularin Macrocycle," Journal of the Chemical Society, Perkin Transactions 1: Organic and Bio-Organic Chemistry, 1997, 17, pp. 2495-2511, ISSN: 0300-922X.

Merrick et al., "Selective Destruction of Stable Mictotubules and Axons by Inhibitors of Protein Serine/Threonine Phosphatases in Cultured Human Neurons (NT2N Cells),"1997, *J Neurosci*, 17:5726-5737.

Miyashita et al, "Synthetic Studies on Fostriecin and Related Natural Products," Yuki Gosei Kagaku Kyokaishi, 2007, 65(9), pp. 874-887, ISSN: 0037-9980. (English Abstract included).

Moller et al., "Okadaic Acid-induced, Naringin-sensitive Phosphorylation of Glycine N-methyltransferase in Isolated Rat Hepatocytes," Biochemical Journal, 2003, 373(2), pp. 505-513, ISSN: 0264-6021.

Moreno et al., "Down-Regulation of the Homeodomain Factor Cdx2 in Colorectal Cancer by Collagen Type I: An Active Role for the Tumor Environment in Malignant Tumor Progression," 2004, *Cancer Res.*, 64:6978-6988.

Mumby, "The 3D Structure of Protein Phosphatase 2A: New Insights into a Ubiquitous Regulator of Cell Signaling," ACS Chemical Biology, 2007, 2(2), pp. 99-103, ISSN: 1554-8929.

Munch et al., "A sensitive and seletive method for the quantitative determination of fatty acid tryptamides as shell indicators in cocoa products," 1999, *Zeitschrift fuer Lebensmittel-Untersuchung und-Forschung A: Food Research and Technology*, 208(1):39-43.

Munch et al., "Characterization of the substances in cocoa shell. Possibilities to determine the shell percentage in cocoa products by indicators," 1999, *Lebensmittelchemie*, 53(6):148.

Nagao et al., "Monitored aminolysis of 3-acylthiazolidine-2-thione: a new convenient synthesis of amide," 1980, *Tetrahedron Letters*, 21(9):841-4.

Nagao et al., "Studies on a new synthesis of the acyclic amide and macrocyclic lactam alkaloids," 1979, *Koen Yoshishu-Tennen Yuki Kagobutsu Torankai*, $22^{nd}$, 554-61 (English language abstract in Appendix A).

Nagao et al., "Utilization of sulfur-containing leavng groups. Part IV. Monitored aminolysis of 3-acyl-1,3-thiazolidine-2-thiones: synthesis of amides and amide alkaloids," 1984, *Chemical & Pharmaceutical Bulletin*, 32(7):2687-99.

Nebesny et al., "Effect of the Roasting Method on the Content of 5-Hydroxytryptamides of Carboxylic Acids in Roasted Coffee Beans," Nahrung, 2002, 46(4), pp. 279-282.

Netland, et al., "Indomethacin Reverses the Microglial Response to Amyloid β-Protein," 1998, *Neurobiology of Aging*, 19(3):201-204.

Neviani et al., "FTY720, a new alternative for treating blast crisis chronic myelogenous leukemia and Philadelphia chromosome-positive acute lymphocytic leukemia," 2007, *J of Clinical Investigation*, 17(9):2408-2421.

Nicholls et al., "Protein Folding and Association: Insights from the Interfacial and Thermodynamic Properties of Hydrocarbons," 1991, *Proteins: Struct. Funct. Genet.*, 11:281-296.

Nien et al., "Overexpression of the mTOR Alpha4 Phosphoprotein Activates Protein Phosphatase 2A and Increases Stat1α Binding to PIAS1," Molecular and Cellular Endocrinology, 2007, 263(1-2), pp. 10-17, ISSN: 0303-7207.

Nishiyama, et al., "Ameliorative Effect of S-Allylcysteine, a Major Thioallyl Constituent in Aged Garlic Extract, on learning Deficits in Senescence-Accelerated Mice," 2001, *American Society for Nutritional Sciences*, 1093S-1095S.

Nowotny et al., "Association studies between common variants in prolyl isomerase *Pin1* and the risk for late-onset Alzheimer's disease," 2007, *Neuroscience Letters*, 419(1):15-7.

Nunbhakdi-Craig et al., "Expression of Protein Phosphatase 2A Mutants and Silencing of the Regulatory Bα Subunit Induce a Selective Loss of Acetylated and Detyrosinated Microtubules," Journal of Neurochemistry, 2007, 101(4), pp. 959-971, ISSN: 0022-3042.

O'Donnell et al., "Serine-threonine Protein Phosphatase Inhibitors Derived from Nodularin: Role of the 2-methyl and 3-diene Groups in the Adda Residue and the Effect of Macrocyclic Conformational Restraint," Journal of the Chemical Society, Perkin Transactions 1, 2001, 14, 1696-1708, ISSN: 1472-7781.

Ogawa et al., "Asymmetric Synthesis of Calyculin C. 2. Synthesis of the C26-C37 Fragment and Model Wittig Couplings," 1996, *Journal of Organic Chemistry*, 61(18):6153-6161, ISSN: 0022-3263.

Ogawa et al., "Total Synthesis of Calyculin C," Journal of the American Chemical Society, 1998, 120(48), pp. 12435-12442, ISSN: 0002-7863.

Ogris et al., "A Protein Phosphatase Methylesterase (PME-1) is One of Several Novel Proteins Stably Associating with Two Inactive Mutants of Protein Phosphatase 2A," Journal of Biological Chemistry, 1999, 274(20), pp. 14382-14391, ISSN: 0021-9258.

Oikawa et al., "Synthetic Study of Tautomycetin and Biological Activity of Tautomycin Derivatives," Tennen Yuki Kagobutsu Toronkai Koen Yoshishu, 1997, 39th, pp. 433-438. (English Abstract included).

Oikawa, "Synthesis of Specific Protein Phosphatase Inhibitors, Tautomycin and Tautomycetin Toward Structure-activity Relationship Study," Current Medicinal Chemistry, 2002, 9(22), pp. 2033-2054, ISSN: 0929-8673.

Ortega-Gutierrez et al., "Targeted Disruption of the PME-1 Gene Causes Loss of Demethylated PP2A and Perinatal Lethality in Mice," PLoS One, 2008, 3(7), e2486, pp. 1-9, ISSN: 1932-6203.

Otvos et al., "Monoclonal Antibody PHF-1 Recognizes Tau Protein Phosphorylated at Serine Residues 396 and 404," 1994, *J. Neurosci Res.*, 39(6):669-673.

Paterson et al, "Total Synthesis of Spirastrellolide a Methyl Ester-part 1: Synthesis of an Advanced C17-C40 Bis-spiroacetal Subunit," Angewandte Chemie, International Edition, 2008, 47(16), pp. 3016-3020, ISSN: 1433-7851.

Peng et al., "Induction of Apoptosis by Norcantharidin in Human Colorectal Carcinoma Cell Lines: Involvement of the CD95 Receptor/Ligand," Journal of Cancer Research and Clinical Oncology, 2002, 128(4), pp. 223-230, ISSN: 0171-5216.

Pihko et al., "Synthesis of the C26-C32 Oxazole Fragment of Calyculin C: A Test Case for Oxazole Syntheses," Journal of Organic Chemistry, 1998, 63(1), pp. 92-98, ISSN: 0022-3263.

Planel et al., "Inhibition of Protein Phosphatase 2A Overrides Tau Protein Kinase I/Glycogen Synthase Kinase 3β and Cyclin-dependent Kinase 5 Inhibition and Results in Tau Hyperphosphorylation in the Hippocampus of Starved mouse," 2001, *J. Biol. Chem.*, 276(36):34298-34306.

Potter, et al., "The inflammation-induced pathological chaperones ACT and apo-E are necessary catalysts of Alzheimer amyloid formation," 2001, *Neurobiology of Aging*, 22:923-930.

Rajagopalan et al., "Molecular Biology of C4 Phosphoenolpyruvate Carboxylase: Structure, Regulation and Genetic Engineering," Photosynthesis Research, 1994, 39(2), pp. 115-135, ISSN: 0166-8595.

Rametti et al., "Linking Alterations in Tau Phosphorylation and Cleavage during Neuronal Apoptosis," 2004, *J. Biol. Chem.*, 279:54518-54528.

Refsum et al., "Homocystein and Cardiovascular Disease," 1998, *Annu. Rev. Medicine*, 49:31-62.

Rizzu et al., "High prevalence of mutations in the microtubule-associated protein tau in a population of study of frontotemporal dementia in the Netherlands," 1999, *Am. J. Hum. Genet.*, 64:414-421.

Roder et al., "Microtubule-associated protein tau as a therapeutic target in neurodegenerative disease," 2007, *Expert Opinion ther. Targets*, 11(4):435-442.

Roszkowski et al., "Enantioselective synthesis of 1-substituted tetrahydro-β-carboline derivatives via asymmetric transfer hydrogenation," 2005, *J. of Molecular Catalysis A: Chemical*, 232(1-2):143-149.

Rusnak et al., "Calcineurin: Form and Function," 2000, *Physiological Reviews*, 80(4):1483-1521.

Ryu et al., 2006, "Photo- and electroluminescent properties of cyano-substituted styryl derivatives and synthesis of CN-PPV model compounds containing an alkoxy spacer for OLEDs," *Tetrahedron*, 62:6236-47.

Sacher et al., "Behenic acid tryptamide, a component of cocoa shell," 1965, *Zeitschrift fuer Lebensmittel-Untersuchung und-Forschung* 128(5):264-7 (English language abstract in Appendix A).

Sakoff & McCluskey, "Protein Phosphatase Inhibition: Structure Based Design. Towards new Therapeutic Agents," 2004, *Current Pharmaceutical Design*, 10:1139-1159.

Sakoff et al., "Anticancer Activity and Protein Phosphatase 1 and 2A Inhibition of a New Generation of Cantharidin Analogues," Investigational New Drugs, 2002, 20(1), pp. 1-11, ISSN: 0167-6997.

Salit et al, "Synthetic Studies Toward Cytostatin, a Natural Product Inhibitor of Protein Phosphatase 2A," Tetrahedron, 2008, 64(28), pp. 6684-6697, ISSN: 0040-4020.

Scarlato et al., "Asymmetric Synthesis of Calyculin C. 1. Synthesis of the C1-C25 Fragment," Journal of Organic Chemistry, 1996, 61(18), pp. 6139-6152, ISSN: 0022-3263.

Schnyder et al., " Decreased Rate of Coronary Restenosis After Lowering of Plasma Homocysteine Levels," 2001, *N Engl J Med*, 345:1593-1600.

Schwartz et al., "Hyperosmotic Stress Contributes to Mouse Colonic Inflammation through the Methylation of Protein Phosphatase 2A," American Journal of Physiology, 2008, 295(5, Pt. 1), pp. G934-G941, ISSN: 0002-9513.

Sciortino et al., "Antiviral activity. IX. Higher acyl derivatives of sympathomimetic amines of biological significance," 1968, *Bollettino Chimico Farmaceutico*, 107(8):506-11.

Scott and Weir, "Folic acid, homocysteine and one-carbon metabolism: a review of the essential biochemistry," 1998, *J Cardiovasc Risk*, 5:223-227.

Scott B., "Protein Phosphatase 2A methylation," 2002, *FEBS Letters*, 518(1-3):1-4.

Selhub et al., "B vitamins, homocysteine, and neurocognitive function in the elderly," 2000, *Am J Clin Nutr*, 71:614S-620S.

Selhub et al., "Vitamin Status and Intake as Primary Determinants of Homocysteinemia in an Elderly Population," 1993, *Jama*, 270:2693-2698.

Selhub, "Homocysteine Metabolism," 1999, *Annu Rev Nutr*, 19:217-246.

Selhub, et al., " Serum Total Homocysteine Concentrations in the Third National Health and Nutrition Examination Survey (1991-1994): Population Reference Ranges and Contribution of Vitamin Status to High Serum Concentrations," 1999, *Ann. Intern. Med.*, 131(5):331-339.

Selkoe, "Alzheimer's Disease: Genes, Proteins, and Therapy," 2001, *Physiol Rev.* 81:741-66.

Seshadri et al., "Plasma Homocystein as a Risk Factor for Dementia and Alzheimer's Disease," 2002, *New England J. of Med.*, 346(7):476.

Sherpina et al., "Ginkgo Biloba," 2003, *American Family Physician*, 68(5):923-926.

Shibasaki et al, "Synthetic Strategies of Fostriecin," Heterocycles, 2005, 66(1), pp. 727-741, ISSN: 0385-5414.

Somei et al., "The chemistry of indoles. 87. Syntheses of 1-hydroxytryptamines and serotonins having fatty acyl or (E)-3-phenylpropenoyl derivatives as a Nb-substituent, and a novel homologation on the 3-substituent of the 1-hydroxytryptamines upon treatment with diazomethane," 1998, *Heterocycles* 48(6):1117-1120.

Sontag et al., "A Novel Pool of Protein Phosphatase 2A Is Associated with Microtubules and Is Regulated during the Cell Cycle," 1995, *J Cell Biol*, 128:1131-1144.

Sontag et al., "Altered Expression Levels of the protein Phosphatase 2A ABαC Enzyme are Associated with Alzheimer Disease Pathology," 2004, *Journal of Neuropathology and Experimental Neurology*, 63(4):287-301.

Sontag et al., "Downregulation of Protein Phosphatase 2A Carboxyl Methylation and Methyltransferase May Contribute to Alzheimer Disease Pathogenesis," Journal of Neuropathology and Experimental Neurology, 2004, 63(10), pp. 1081-1091, ISSN: 0022-3069.

Sontag et al., "Molecular Interactions among Protein Phosphatase 2A, Tau, and Microtubules," 1999, *J. Biol. Chem.*, 274(36):25490-25498.

Sontag et al., "Protein Phosphatase 2A Methyltransferase Links Homocysteine Metabolism with Tau and Amyloid Precursor Protein Regualtion," Journal of Neuroscience, 2007, 27(11), pp. 2751-2759, ISSN: 0270-6474.

Sontag et al., "Regulation of Phosphorylation State and Microtubule-Binding Activity of tau by Protein Phosphatase 2A," 1996, *Neuron*, 17:1201-1207.

Sontag, E. "Protein phosphatatase 2A: the Trojan Horse of Cellular signaling," 2001, *Cell. Signaling*, 13:7-16.

Stock et al., "A protein methylesterase involved in bacterial sensing," 1978, *Proc. Natl. Acad. Sci. USA*, 75(8):3659-3663.

Stone et al., "Molecular Cloning of cDNAs Encoding Two Isoforms of the Catalytic Subunit of Protein Phosphatase 2A," 1987, *Biochemistry*, 26:7215-7220.

Studer et al., "Quantitative HPTLC Determination of Carbon-5-Hydroxytryptamides and-Tryptamines in Food Products," Journal of High Resolution Chromatography & Chromatography Communications, Oct. 1982, vol. 5(No. 10358), pp. 581-582.

Sun et al., "Inhibition of Protein Phosphatase 2A- and Protein Phosphatase 1-Induced Tau Hyperphosphorylation and Impairment of Spatial Memory Retention in Rats," 2003, *Neuroscience*, 118:1175-1182.

Sunahori et al., "Methylation Status of CpG Islands Flanking a cAMP Response Element Motif on the Protein Phosphatase 2Acα Promoter Determines CREB Binding and Activity," Journal of Immunology, 2009, 182(3), pp. 1500-1508, ISSN: 0022-1767.

Swiatek et al., "Biochemical Characterization of Recombinant Subunits of Type 2A Protein Phosphatase Overexpressed in *Pichia pastoris*," European Journal of Biochemistry, 2000, 267(16), pp. 5209-5216, ISSN: 0014-2956.

Szelag et al., "Determination of the amount of hull-derived lipids in cocoa oils," 1984, *Przemysl Spozywczy* 38(9):355-7.

Szelag et al., "Evaluation of behenic acid tryptamide in cocoa fat on the basis of blue value dterminations," 1988, *Nahrung*, 32(3):285-90.

Taylor et al., "Potent Non-peptidyl Inhibitors of Protein Tyrosine Phosphatase 1B," Bioorganic & Medicinal Chemistry, 1998, 6(9), pp. 1457-1468, ISSN: 0968-0896.

Taylor et al., "Potent Non-peptidyl Inhibitors of Protein Tyrosine Phosphatase 1B. [Erratum to document cited in CA130:3892]," Bioorganic & Medicinal Chemistry, 1998, 6(11), pp. 2235, ISSN: 0968-0896.

Tolstykh et al., "Carboxyl Methylation Regulates Phosphoprotein Phosphatase 2A by Controlling the Association of Regulatory B Subunits," EMBO Journal, 2000, 19(21), pp. 5682-5691, ISSN: 0261-4189.

Travesa et al., "Distinct Phosphatases Mediate the Deactivation of the DNA Damage Checkpoint Kinase Rad53," Journal of Biological Chemistry, 2008, 283(25), pp. 17123-17130, ISSN: 0021-9258.

Tsujio et al., "Inhibitors of protein phosphatase-2A from human brain structures, immunocytological localization and activities towards dephosphorylation of the Alzheimer type hyperphosphorylated tau," 2005, *FEBS Lett*, 579:363-372.

Turowski et al., "Differential Methylation and Altered Conformation of Cytoplasmic and Nuclear Forms of Protein Phosphatase 2A During Cell Cycle Progression," Journal of Cell Biology, 1995, 129(2), pp. 397-410, ISSN: 0021-9525.

Tverdal et al., "Coffee Intake and Mortality from Liver Cirrhosis," 2003, *AEP* 13(6):419-423.

Tyas, S., "Are tobacco and alcohol use related to Alzheimer's disease? a critical assessment of the Evidence and its Implications" 1996, *Addiction Biology*, 1(3):237.

Urban, 1959, "Physiology of some flavonoids and oxycinnamic acid. II. Annual and diurnal periodicity of formation," *Planta*, 52:565-82.

Vafai et al., "Protein phosphatase 2A methylation: a link between elevated plasma homocysteine and Alzheimer's Disease," 2002, FEBS Letters, 518:1-4.

Van Dam et al., "Coffee consumption and risk of type 2 diabetes mellitus," 2002, *The Lancet*, 360:1477.

Virshup, D., "Protein phosphatase 2A:a panoply of enzymes," 2000, *Curr Opin. Cell Biol.*, 12:180-185.

Vogelsberg-Ragaglia et al., "PP2A mRNA Expression Is Quantitatively Decreased in Alzheimer's Disease Hippocampus," 2001, *Exp Neurol*, 168:402-412.

Wang et al., "Inhibition of Growth and p21*ras* Methylation in Vascular Endothelial Cells by Homocysteine but Not Cysteine," 1997, *J Biol Chem*, 272:25380-25385.

Webster et al., "Design and Preparation of Serine-Threonine Protein Phosphatase Inhibitors Based Upon the Nodularin and Microcystin Toxin Structures. Part 3," Journal of the Chemical Society, Perkin Transactions 1, 2001, 14, pp. 1673-1695, ISSN: 1472-7781.

Wei et al., "Carboxymethylation of the PP2A Catalytic Subunit in *Saccharomyces cerevisia* is Required for Efficient Interaction with the B-type Subunits Cdc55p and Rts1p," Journal of Biological Chemistry, 2001, 276(2), pp. 1570-1577, ISSN: 0021-9258.

Welch, G.N. and Loscalzo, J., "Homocysteine and Atherothrombosis," 1998, *N Engl J Med*, 338:1042-1050.

Wera et al., "Serine/threonine protein phosphatases," 1995, *Biochem. J.*, 311:17-19.

Wiart et al., "Sesquiterpenes and Alkaloids from Scorodocarpus Borneensis," Phytochemistry, 2001, 58(4), pp. 653-656.

Williams et al., "Spirastrellolide A: A Revised Structure, Progress Toward the Relative Configuration, and Inhibition of Protein Phosphatase 2A," Organic Letters, 2004, 6(15), pp. 2607-2610, ISSN: 1523-7060.

Witten Opinion for PCT/US09/41321, Jun. 1, 2009.
Written Opinion for PCT/US2006/003686, Aug. 2, 2007.
Written Opinion for PCT/US2007/81260, Sep. 11, 2008.
Written Opinion for PCT/US2007/82833, Oct. 9, 2008.

Wu et al., "Carboxyl Methylation of the Phosphoprotein Phosphatase 2A Catalytic Subunit Promotes its Functional Association with Regulatory Subunits in vivo," 2000, *EMBO*, 19(21):5672-5681.

Wu et al., "Tryptamine-Derived Amides and Alkaloids from the Seeds of Annona atemoya," 2005, *J. of Natual Products*, 68(3):406-408.

Wurziger at al., "Hydroxytrypatamides of Green and Roasted Coffee Beans," Presented at Association Scientifique Internationale du Cafe, 4th International Colloquium on the Chemistry of Coffee, 1969, pp. 85-91.

Wurziger et al., "Chemistry of Cocoa. Carboxylic Acid-5-Hydroxytryptamide in Cocoa Beans," 1970, *Hyg. Inst., Gordian*, 70(1644), Part 2:438-440.

Wurziger et al., "Chemistry of Cocoa. Carboxylic Acid-5-Hydroxytryptamide in Cocoa Beans," 1970, *Hyg. Inst., Gordian*, 70(1645), Part 3:470-473.

Wurziger et al., "Chemistry of Cocoa. Carboxylic Acid-5-Hydroxytryptamide in Cocoa Beans," 1970, *Hyg. Inst., Gordian*, 70(1643), Part 1:376-378.

Xie and Clarke, 1993, "Methyl esterification of C-terminal leucine residues in cytosolic 36-kDa polypeptides of bovine brain," *J. Biol. Chem.*, 268(18):13364-71.

Xie et al., "An Enzymic Activity in Bovine Brain that Catalyzes the Reversal of the C-terminal Methyl Esterification of Protein Phosphatase 2A," Biochemical and Biphysical Research Communications, 1994, 203(3), pp. 1710-1715, ISSN: 0006-291X.

Xie et al., "Protein Phosphatase 2A is Reversibly Modified by Methyl Esterification at its C-terminal Leucine Residue in Bovine Brain," Journal of Biological Chemistry, 1994, 269(3), pp. 1981-1984, ISSN: 0021-9258.

Xing et al., "Structural Mechanism of Demethylation and Inactivation of Protein Phosphatase 2A," Cell, 2008, 133(1), pp. 154-163, ISSN: 0092-8674.

Xing et al., "Structure of protein phosphatase 2A core enzyme bound to tumor-inducing toxins," 2006, *Cell*, 127(2):341-353.

Xu et al., "Structure of the Protein Phosphatase 2A Holoenzyme," 2006, *Cell*, 127(6):1239-1251.

Yang et al., "S-adenosylemthionine and its Metabolite Induce Apoptosis in HepG2 Cells: Role of Protein Phosphatase 1 and BcI-xS," Hepatology, 2004, 40(1), pp. 221-231, ISSN: 0270-9139.

Yi et al., "Increase in Plasma Homocysteine Associated with Parallel Increase in Plasma S-Adenosylhomocysteine and Lymphocyte DNA Hypomethylation," 2000, *J Biol Chem*, 275:29318-29323.

Yoo et al., "The α4-containing Form of Protein Phosphatase 2A in Liver and Hepatic Cells," Journal of Cellular Biochemistry, 2008, 105(1), pp. 290-300, ISSN: 0730-2312.

Yoon et al., "Methotrexate Decreases PP2A Methylation and Increases Tau Phosphorylation in Neuron," Biochemical and Biophysical Research Communications, 2007, 363(3), pp. 811-816, ISSN: 0006-291X.

Yu et al., "Methylation of the Protein Phosphatase 2A Catalytic Subunit is Essential for Association of Bα Regulatory Subunit but not SG2NA, Striatin, or Polyomavirus Middle Tumor Antigen," Molecular Biology of the Cell, 2001, 12(1), pp. 185-199, ISSN: 1059-1524.

Zhang et al., "Homocysteine Induces Tau Phosphorylation by Inactivating Protein Phosphatase 2A in Rat Hippocampus," Neurobiology of Aging, 2008, 29(11), pp. 1654-1665, ISSN: 0197-4580.

Zhou et al., "Tau Hyperphosphorylation Correlates with Reduced Methylation of Protein Phosphatase 2A," Neurobiology of Disease, 2008, 31(3), pp. 386-394, ISSN: 0969-9961.

Buée et al., Brain Res Brain Res Rev 33(1): 95, (2000).

Planel et al., J Biol Chem. 276(36):34298, (2001).

Janssens, V., Gloris, J., Biochem. J. 353 (Pt. 3): 417, (2001).

Kamibayashi, C. et al., J. Biol. Chem. 269 (31): 20139, (1994).

Sontag, E., et al., J. Neuropathol. Exp. Neurol. 63 (4): 287, (2004).

Tolstykh, T. et al., EMBO J. 19 (21): 5682, (2000).

Wu , J. et al., EMBO J. 19 (21): 5672, (2000).

Wei, H. et al., J. Biol. Chem. 276 (2): 1570, (2001).

Yu, Xx, et al., Mol. Biol. Cell 12 (1): 185, (2001).

Vafai, S.B., Stock, J.B., FEBS Lett. 518 (1-3): 1-4 (2002).

Selhub J., et al., Ann. Intern. Med. 131 (5): 331-39 (1999).

New England Journal of Medicine, 346 (7): 476-83 (2002).

Lindsay et al., Am J Epidemiol. 156(5):445-53 (2002).

Lee, J., Stock, J., J. Biol. Chem. 268 (26) 19192-195 (1993).

\* cited by examiner

COMPOSITIONS AND METHODS FOR ENHANCING COGNITIVE FUNCTION

CROSS REFERENCE TO RELATED APPLICATIONS

This application claims the benefit of priority of U.S. Provisional Application No. 60/649,902 entitled "Enhancing Cognitive Function," filed Feb. 3, 2005. The entire disclosure of this application is incorporated by reference.

GOVERNMENT RIGHTS

This work is supported at least in part by grants to Dr. Jeffry Stock. The government may have certain rights in this invention.

FIELD OF THE INVENTION

The present invention relates to treatment or prevention of human disease and to the enhancement of the general health or well-being of a human subject using compositions extracted from herbs and other botanical and microbial materials.

BACKGROUND OF THE INVENTION

Alzheimer's disease (AD) is one of the most prevalent of progressive brain disorders. Currently an estimated 4.5 million older Americans suffer from AD. According to the latest estimates of the current and future prevalence of AD, the number of older people with AD will grow dramatically as the population ages. Projections indicate that as many as 13 million older Americans will have AD by 2050 unless new ways are found to prevent or treat the disease. AD is currently the third most expensive disease after heart disease and cancer. Treatment and care of those with AD now runs $100 to $150 billion a year and costs are projected to rise sharply as the population ages. Currently, pharmacological treatment of AD is primarily based on the use of acetylcholinesterase inhibitors (AChEIs), which have been reported to provide beneficial effects on cognitive, functional, and behavioral symptoms of the disease. Four of the five drugs approved for AD treatment in the U.S.—donepezil (Aricept®), rivastigmine (Exelon®), galantamine (Reminyl®), and tacrine (Cognex®)—are AChEIs. The fifth, Mementine (Namenda®), is an N-methyl-D-aspartate ("NMDA") antagonist that alters glutamate signaling. Because only a small fraction of AD patients respond to this type of treatment, any new approach to the treatment or prevention of AD would have tremendous value. In spite of intensive research, there are no proven preventive agents or agents capable of limiting progression of the disease, and the few used to ameliorate its symptoms have side effects of nausea, vomiting, diarrhea, and even liver damage, yet do not meaningfully slow the disease's underlying course for most patients. AD may well be the most pharmaceutically under-served major disease in the US.

AD is physically evidenced by amyloid plaques and neurofibrillary tangles in the brain. These pathological markers are associated with cognitive regression and other varied symptoms of the disease. The amyloid plaques, which are the focus of the preponderance of research today on the disease, contain aggregated amyloid β-peptides derived from proteolytic cleavage of the larger amyloid precursor protein. The major component of neurofibrillary tangles is the protein tau, a constituent of the cytoskeleton. Tau is a microtubule-associated protein that functions in brain to regulate the structure and function of axonal microtubules. Over the past decade, several groups have demonstrated that the tau protein found in neurofibrillary tangles is hyperphosphorylated. Tau hyperphosphorylation is thought to destabilize microtubules and thereby contribute to neurodegenertion and the development of AD. Tau hyperphosphorylation results from an imbalance between kinase and phosphatase activities (reviewed in Buee et al., *Brain Res Brain Res Rev* 33(1): 95-130 (2000)). Several serine/threonine protein kinases have been implicated in tau phosphorylation including cyclin-dependent kinase 5 ("cdk-5"), glycogen synthase kinase-3b ("GSK-3b") and MAP kinases. Tau dephosphorylation appears to be primarily mediated by protein phosphatase 2A ("PP2A"). Importantly, recent results suggest that a decrease in PP2A activity is associated with the elevated levels of tau phosphorylation that appear to cause neurofibrillary tangle formation (Planel et al., *J Biol Chem.* 276(36):34298-306 (2001)). Enhancement of this activity therefore may have significant therapeutic value. Since PP2A methylation greatly enhances the formation of a PP2A heterotrimer, it is believed that enhancing PP2A methylation will result in enhanced PP2A activity towards Tau.

Protein phosphatase 2A (PP2A) associates with a variety of regulatory subunits. (Janssens, V., Gloris, J., *Biochem. J.* 353 (Pt. 3): 417-39 (2001)). The predominant form in neuronal tissue is a trimer composed of a dimeric core composed of a 65 kilodalton (kDa) A subunit and the 36 kDa PP2A catalytic C subunit associated with one of several different regulatory B subunits. Whereas the A and C subunits are present more or less uniformly, the B subunit is variable and confers substrate specificity and subcellular localization to each PP2A holoenzyme trimer. The number and types of B subunits present is subject to developmental regulation and is cell type specific.

The variable B subunits of PP2A are classified into four families: (1) the B family with four isoforms ($\alpha$, $\beta$, $\gamma$, $\delta$); (2) the B' family with five isoforms ($\alpha$, $\beta$, $\gamma$, $\delta$, $\epsilon$); (3) the B'' family; and (4) the B''' family. The PP2A $AB_\alpha C$ heterotrimer appears to be the major phosphatase in brain responsible for dephosphorylation of tau. (Kamibayashi, C. et al., *J. Biol. Chem.* 269 (31): 20139-148 (1994); Sontag, E., et al., *J. Neuropathol. Exp. Neurol.* 63 (4): 287-301 (2004)).

The alpha-carboxyl of the C terminal leucine residue of the catalytic subunit of PP2A is subject to methyl esterification and methyl-ester hydrolysis, and the methylation state of PP2A regulates heterotrimer formation. (Tokstykh, T. et al., *EMBO J.* 19 (21): 5682-91 (2000); Wu, J. et al., *EMBO J.* 19 (21): 5672-81 (2000); Wei, H. et al., *J. Biol. Chem.* 276 (2): 1570-77 (2001); Yu, X X, et al., *Mol. Biol. Cell* 12 (1): 185-99 (2001)). Two enzymes are involved in controlling the methylation state of PP2A: (1) an S-adenosylmethionine-dependent PP2A-specific protein methyltransferase ("PPMT"), which adds the methyl group and (2) a PP2A-specific protein methylesterase ("PPME"), which removes the methyl group. PP2A methylation promotes PP2A $AB_\alpha C$ trimer assembly. Any deficiency in methylation is expected to preclude PP2A $AB_\alpha C$ heterotrimer formation, thereby leading to a deficiency in tau dephosphorylation, tau hyperphosphorylation and the formation of neurofibrillary tangles. (Vafai, S. B., Stock, J. B., *FEBS Lett.* 518 (1-3): 1-4 (2002)).

Homocysteine, a sulfur-containing amino acid that can be either remethylated to methionine or undergo a trans-sulfuration reaction to cystathionine, plays a key role in methylation metabolism (see FIG. 1). The conversion of homocysteine to methionine occurs in all tissues. Methionine is activated by ATP in the presence of methionine adenosyl transferase (labeled as (1) in FIG. 1) to form the methyl donor, S-adenosylmethionine ("SAM"). SAM-dependent methylation reactions in the presence of SAM-dependent methyltransferases (labeled as (2) in FIG. 1) result in the formation of S-adenosylhomocysteine ("SAH"), which is cleaved by SAH hydrolase (labeled as (3) in FIG. 1) to form adenosine and homocysteine. This reaction is reversible with the equilibrium favoring the condensation of homocysteine and adenosine. Under normal conditions, homocysteine is rapidly methylated, which favors the further cleavage of SAH. Homocysteine accumulation leads to global decreases in cellular methylation by the condensation of homocysteine with adenosine to form SAH, which acts as a product inhibitor in cellular methylation reactions. In the United States, 5-10% of the general population has elevated plasma homocysteine, and this imbalance increases to 30-40% in of the elderly. (Selub J., et al., *Ann. Intern. Med.* 131 (5): 331-39 (1999)). The enzymes cystathionine L-synthase; cystathionine Q lyase; betaine homocysteine methyltransferase; and methionine synthase are labeled as (4), (5), (6) and (7), respectively in FIG. 1. See Vafai, S. B., Stock, J. B., FEBS Lett. 2: 518 (2002).

Over the last several years, data has emerged in clinical literature suggesting a direct association between elevated plasma homocysteine and the occurrence of AD. Seshadri et al., (*N Engl J Med* 346 (7): 476-83 (2002)), demonstrated that elevated homocysteine is a risk factor for AD. After adjusting for other AD risk factors, the study concluded that plasma homocysteine levels greater than 14 µM coincided with about a 2-fold increased risk for developing AD with an additional 40% increased risk with each 5 µM incremental rise. Other diseases, conditions or disorders associated with elevated plasma homocysteine include, but are not limited to, atherosclerosis; neurodegenerative disorders, such as Parkinson's disease; cerebrovascular disorders (i.e., disorders pertaining to blood vessels in the brain), such as stroke; neuropsychiatric disorders, such as bipolar disorder and schizophrenia; diabetes (type II), and arthritis.

An analysis of the clinical and basic science literature indicates that a methylation defect resulting from elevated homocysteine could lead to lowered levels of PP2A methylation that would result in lowered PP2A $AB_\alpha C$, which is believed to lead to tau hyperphosphorylation, neurofibrillary tangle formation, and dementia (Vafai and Stock, *FEBS Lett* 518(1-3): 1-4 (2002)).

Cellular pathways for removing plasma homocysteine require folate, Vitamin B6 and B12, and thus high homocysteine levels are expected in mice fed diets deficient in these components. This was demonstrated using, male C57BL/J6 mice. One set of 4 week old mice were placed on a diet that contained folate, vitamin B6, and vitamin B12 and another set were fed diets that lacked these vitamins. The mice were allowed free access to both food and water. After nine weeks on their respective diets, each mouse was sacrificed by cervical dislocation. Blood samples were collected for measurement of plasma homocysteine and the brain was removed and quickly frozen in liquid nitrogen for further analysis of tau phosphorylation. As expected the vitamin-deficient diets caused substantial increases in plasma Hcy and brain SAH. These increases were accompanied by elevated levels of Tau phosphorylation, as shown in FIG. 2 FIG. 2 provides Western blots after SDS-PAGE of extracts prepared from the brains of mice raised on normal diets (A and B) and vitamin-deficient diets (C and D). CP13 and PHF1 are monoclonal antibodies that are specific for phosphorylated tau epitopes. TG5 is a monoclonal antibody that recognizes tau independent of its state of phosphorylation; it thereby provides a control showing that total levels of tau expression are unaffected by diet. Mice raised on diets deficient in folate, B12, and B6 had dramatically elevated levels of total plasma homocysteine, brain S-adenosyl homocysteine and elevated levels of tau phosphorylation. S-Adenosyl methionine levels were not significantly affected.

The demographics of aging in the United States population, combined with a lack of effective treatments, have heightened the need for AD therapies. Moreover, the development of preventives would be an even greater contribution to public health. A protective agent that could be taken over many years to reduce the risk of AD or to substantively delay its onset would be an invaluable breakthrough.

Coffee has been used for centuries by a diverse range of populations and is presently the most popular beverage worldwide with over 400 billion cups consumed each year. There are many anecdotal reports of the medicinal value of coffee but in spite of its worldwide prevalence, little is really known about its potential medical uses. Some epidemiological studies have suggested an inverse association between coffee consumption and the risk not only of AD, but also of liver cirrhosis, colorectal cancer, cardiovascular mortality, type 2 diabetes and Parkinson's disease. Recent studies have suggested that coffee consumption reduces the risk for AD by as much as 30% (Lindsay et al., Am J Epidemiol. 156(5):445-53 (2002)). Various mechanisms for the purported benefits have been suggested, but none have been explored fully enough for these suggestions to be definitive. Moreover, brewed coffee is a complex mixture that contains several pharmacologically active components, including caffeine.

The present invention provides a definitive mechanism, i.e., enhancement of PP2A methylation, by which to measure benefit to a subject's health and general well-being, and, in particular, cognitive function. An agent that increases the levels of PP2A methylation would help maintain high levels of PP2A ABC heterotrimer formation and may thereby prevent the demethylation of PP2A and the lowered levels of PP2A ABC heterotrimers that have been associated with tau hyperphosphorylation, neurofibrillary tangle formation, and neurodegeneration in AD.

SUMMARY OF THE INVENTION

The present invention provides novel compositions that inhibit PP2A demethylation and thereby prevent negative effects of PP2A demethylation associated with diseases such as AD and methods to prepare these compositions. According to one embodiment of the present invention, a composition for promoting general health and well-being in a mammalian subject, including a human, comprises an isolated methylation modifying compound. According to another embodiment, the compound of the composition is isolated from a botanical raw material. According to another embodiment, the compound of the composition is isolated from a microbial raw material. According to another embodiment, the composition inhibits a demethylating activity of a demethylating enzyme that acts on a protein phosphatase 2A enzyme and thereby stimulates methylation of the protein phosphatase 2A enzyme. According to another embodiment, the composition inhibits at least about 50% of the demethylating activity of the demethylating enzyme. According to another embodiment, the demethylating enzyme is a protein phosphatase 2A specific protein methylesterase. According to another embodiment, the demethylating activity of the protein phosphatase 2A specific protein methylesterase is determined by measuring levels of protein phosphatase 2A methyl esterification. According to another embodiment, the botanical raw material comprises at least one substance selected from the group consisting of gingko, allicin, bacopa; butcher's broom; flaxseed oil; a tocopherol; vitamin E; ginseng, grape seed, St. John's wort; artichoke-powder; choline; inositol; coffee; tea; tobacco; and cocoa. According to another embodiment, the botanical raw material comprises a fruit of a species of plant genus *Coffea*. According to another embodiment, the fruit of the plant genus *Coffea* is a coffee bean. According to another embodiment, the botanical raw material comprises a nutritional supplement. According to another embodiment, the nutritional supplement comprises at least one tocopherol. According to another embodiment, the nutritional supplement comprises Vitamin E. According to another embodiment, the botanical raw material comprises a leaf of a tobacco plant. According to another embodiment, the botanical raw material comprises a ground coffee or an instant coffee. According to another embodiment, the methylation modifying compound is isolated from the botanical raw material by extracting the botanical raw material with a polar solvent. According to another embodiment, the polar solvent is a lower alcohol. According to another embodiment, the lower alcohol is ethanol. According to another embodiment, the polar solvent is ethyl acetate. According to another embodiment, the methylation modifying compound is soluble in ethyl acetate below a pH of about 5 and insoluble in ethyl acetate above a pH of about 10. According to another embodiment, the composition is essentially free of at least one substance selected from the group consisting of caffeine, caffeic acid and chlorogenic acid.

According to yet another embodiment of the present invention, a comestible for promoting general health and well-being in a mammalian subject, including a human, comprises a composition containing an isolated methylation modifying compound. According to another embodiment, the compound is isolated from a botanical raw material. According to another embodiment, the compound is isolated from a microbial raw material. According to another embodiment, the composition inhibits a demethylating activity of a demethylating enzyme that acts on a protein phosphatase 2A enzyme and thereby stimulates methylation of the protein phosphatase 2A enzyme. According to another embodiment, the composition inhibits at least about 50% of the demethylating activity of the demethylating enzyme. According to another embodiment, the demethylating enzyme is protein phosphatase 2A specific protein methylesterase. According to another embodiment, the level of protein methylesterase demethylating activity is determined by measuring levels of protein phosphatase 2A methyl esterification. According to another embodiment, the botanical raw material comprises at least one substance selected from the group consisting of gingko, allicin, bacopa; butcher's broom; flaxseed oil; a tocopherol; vitamin E; ginseng, grape seed, St. John's wort; artichoke-powder; choline; inositol; coffee; tea; tobacco; and cocoa. According to another embodiment, the botanical raw material comprises a fruit of a species of plant genus *Coffea* According to another embodiment, the fruit of the plant genus *Coffea* is a coffee bean. According to another embodiment, the botanical raw material comprises a nutritional supplement. According to another embodiment, the nutritional supplement comprises at least one tocopherol. According to another embodiment, the nutritional supplement comprises Vitamin E. According to another embodiment, the botanical raw material comprises a leaf of a tobacco plant. According to another embodiment, the botanical raw material comprises a ground coffee. According to another embodiment, the botanical raw material comprises an instant coffee. According to another embodiment, the methylation modifying compound is isolated from the botanical raw material by extracting the botanical raw material with a polar solvent. According to another embodiment, the polar solvent is a lower alcohol. According to another embodiment, the lower alcohol is ethanol. According to another embodiment, the polar solvent is ethyl acetate. According to another embodiment, the methylation modifying compound is soluble in ethyl acetate below a pH of about 5 and insoluble in ethyl acetate above a pH of about 10. According to another embodiment, the composition is essentially free of at least one substance selected from the group consisting of caffeine, caffeic acid and chlorogenic acid. According to another embodiment, the comestible is a beverage. According to another embodiment, the beverage is selected from the group consisting of a drink comprising water, a fruit drink, a coffee, a tea, an energy drink, a baby formula, an adult nutritional drink, a health drink, and a sports drink. According to another embodiment, the comestible is a food. According to another embodiment, the comestible is a cereal. According to another embodiment, the comestible is a chewing gum. According to another embodiment, the comestible is a candy. According to another embodiment, the comestible is an ingredient of an inhalant. According to another embodiment, the comestible is an ingredient of a transdermal delivery system.

According to yet another embodiment of the present invention, a pharmaceutical preparation for promoting general health and well-being in a mammalian subject, including a human, comprises a cognitive function-enhancing amount of a composition containing an isolated methylation modifying compound and a pharmaceutically acceptable carrier. According to another embodiment, the compound is isolated from a botanical raw material. According to another embodiment, the compound is isolated from microbial raw material. According to another embodiment, the compound inhibits a demethylating enzyme that acts on a protein phosphatase 2A and thereby stimulates methylation of the protein phosphatase 2A enzyme. According to another embodiment, the composition inhibits at least about 50% of the demethylating activity of the demethylating enzyme. According to another embodiment, the demethylating enzyme is a protein phosphatase 2A specific protein methylesterase. According to another embodiment, the demethylating activity of the protein phosphatase 2A specific protein methylesterase is determined by measuring levels of protein phosphatase 2A methyl esterification. According to another embodiment, the botanical raw material comprises at least one substance selected from the group consisting of gingko; allicin, bacopa; butcher's broom; flaxseed oil; a tocopherol; vitamin E; ginseng, grape seed, St. John's wort; artichoke-powder; choline, inositol; tea; tobacco; and cocoa. According to another embodiment, the botanical raw material comprises a fruit of a species of plant genus *Coffea*. According to another embodiment, the fruit of the plant genus *Coffea* is a coffee bean. According to another embodiment, the botanical raw material comprises a ground or instant coffee. According to another embodiment, the botanical raw material is a nutritional supplement. According to another embodiment, the nutritional supplement comprises at least one tocopherol. According to another embodiment, the nutritional supplement comprises vitamin E. According to another embodiment, the botanical raw material comprises a leaf of a tobacco plant. According to another embodiment, the methylation modifying compound is isolated from the botanical raw material by extracting the botanical raw material with a polar solvent. According to another embodiment, the polar solvent is a lower alcohol. According to another embodiment, the lower alcohol is ethanol. According to another embodiment, the polar solvent is ethyl acetate. According to another embodiment, the methylation modifying compound is soluble in ethyl acetate below a pH of about 5 and insoluble in ethyl acetate above a pH of about 10. According to another embodiment, the pharmaceutical preparation is essentially free of at least one substance selected from the group consisting of caffeine, caffeic acid and chlorogenic acid. According to another embodiment, the preparation is administered orally. According to another embodiment, the preparation is in the form of a powder. According to another embodiment, the preparation is in the form of a tablet, a capsule, a lozenge, or a suppository.

According to yet another embodiment of the present invention, a method for promoting general health and well-being in a mammalian subject, including a human, the method comprises the steps (a) isolating a methylation modifying compound; and (b) administering a cognitive function-enhancing amount of a composition comprising the isolated methylation modifying compound to a subject in need thereof. According to another embodiment, in step (a), the methylation modifying compound is isolated from a botanical raw material. According to another embodiment, in step (a) the methylation modifying compound is isolated from a microbial raw material. According to another embodiment, the methylation modifying compound inhibits a demethylating enzyme that acts on a protein phosphatase 2A enzyme and thereby stimulates methylation of the protein phosphatase 2A enzyme. According to another embodiment, the composition inhibits at least about 50% of the demethylating activity of the demethylating enzyme. According to another embodiment, the demethylating enzyme is a protein phosphatase 2A specific protein methylesterase. According to another embodiment, the method further comprises the step of (c) determining the demethylating activity of the protein phosphatase 2A specific protein methylesterase. According to another embodiment, the cognition function-enhancing amount of the composition is from about 1 mg to about 10 g. According to another embodiment, the botanical raw material comprises at least one substance selected from the group consisting of gingko, allicin, bacopa; butcher's broom; flaxseed oil; a tocopherol; vitamin E; ginseng, grape seed, St. John's wort; artichoke-powder; choline; inositol; tea; tobacco; and cocoa. According to another embodiment, the botanical raw material comprises a fruit of a species of plant genus *Coffea*. According to another embodiment, the fruit of the plant genus *Coffea* is a coffee bean. According to another embodiment, the botanical raw material comprises a ground or instant coffee. According to another embodiment, the botanical raw material comprises a nutritional supplement. According to another embodiment, the nutritional supplement comprises at least one tocopherol. According to another embodiment, the nutritional supplement comprises vitamin E. According to another embodiment, the botanical raw material comprises a leaf of a tobacco plant. According to another embodiment, step (a) further comprises the step of extracting the botanical raw material with a polar solvent. According to another embodiment, the polar solvent is a lower alcohol. According to another embodiment, the lower alcohol is ethanol. According to another embodiment, the polar solvent is ethyl acetate. According to another embodiment, step (a) further comprises the steps of solubilizing the methylation modifying compound in ethyl acetate below a pH of about 5 and partitioning the methylation modifying compound between an aqueous phase and ethyl acetate above a pH of about 10. According to another embodiment, the extracted composition is essentially free of at least one substance selected from the group consisting of caffeine, caffeic acid and chlorogenic acid. According to another embodiment, in step (b), the composition is administered orally. According to another embodiment, the composition is a powder, tablet, capsule, lozenge or suppository.

According to yet another embodiment of the present invention, a composition for promoting general health and well-being in a mammalian subject, including a human, is prepared by a process, which comprises the steps: a) contacting a botanical raw material with a polar solvent for a time sufficient to form an extract solution from the botanical raw material; b) isolating the extract solution and removing the polar organic solvent to form a concentrated primary extract; and c) dissolving the composition in a solvent at a pH ranging from about 7 to about 10 to form a concentrated purified extract. According to another embodiment, the polar solvent in step (a) of the process is a lower alcohol. According to another embodiment, the lower alcohol is ethanol. According to another embodiment, the polar solvent in step (a) of the process is ethyl acetate. According to another embodiment, step (a) of the process further comprises the step of solubilizing the composition in ethyl acetate below a pH of about 5. According to another embodiment, step (b) of the process further comprises the step of partitioning the methylation modifying compound between an aqueous phase and ethyl acetate above a pH of about 10. According to another embodiment, the composition inhibits a demethylating activity of a demethylating enzyme that acts on a protein phosphatase 2A enzyme and thereby stimulates methylation of the protein phosphatase 2A enzyme. According to another embodiment, the composition inhibits at least about 50% of the demethylating activity of the demethylating enzyme. According to another embodiment, the demethylating enzyme is a protein phosphatase 2A specific protein methylesterase. According to another embodiment, the botanical raw material comprises at least one substance selected from the group consisting of gingko; allicin; bacopa; butcher's broom; flaxseed oil; a tocopherol; vitamin E; ginseng; grape seed; St. John's wort; artichoke-powder; choline; inositol; coffee; tea; tobacco; and cocoa. According to another embodiment, the botanical raw material comprises a fruit of a species of plant genus *Coffea*. According to another embodiment, the fruit of the plant genus *Coffea* is a coffee bean. According to another embodiment, the botanical raw material comprises a ground or instant coffee. According to another embodiment, the botanical raw material comprises a nutritional supplement. According to another embodiment, the nutritional supplement comprises at least one tocopherol. According to another embodiment, the nutritional supplement comprises Vitamin E. According to another embodiment, the botanical raw material comprises a leaf of a tobacco plant. According to another embodiment, the concentrated purified extract is essentially free of at least one substance selected from the group consisting of caffeine, caffeic acid and chlorogenic acid. According to another embodiment, the composition is administered orally. According to another embodiment, the composition is in the form of a powder, a tablet, a capsule, a lozenge or a suppository.

According to yet another embodiment of the present invention, a method of treating or preventing cognitive effects of a disease, condition, or disorder involving defective methylation metabolism in a mammalian subject, including a human, comprises the steps of (a)

isolating a methylation modifying compound; and (b) administering a therapeutically effective amount of a composition comprising the isolated methylation modifying compound to a subject in need thereof. According to another embodiment, in step (a) the methylation modifying compound is isolated from a botanical raw material. According to another embodiment, in step (a) the methylation modifying compound is isolated from a microbial raw material. According to another embodiment, the disease, condition, or disorder is associated with higher than normal levels of plasma homocysteine. According to another embodiment, the disease condition or disorder is at least one disease, condition or disorder selected from the group consisting of a cardiac disorder; atherosclerosis; a neurodegenerative disorder; a cerebrovascular disorder; a neuropsychiatric disorder; and diabetes. According to another embodiment, the methylation modifying compound inhibits a demethylating activity of a demethylating enzyme that acts on a protein phosphatase 2A enzyme and thereby stimulates methylation of the protein phosphatase 2A enzyme. According to another embodiment, the composition inhibits at least about 50% of the demethylating activity of the demethylating enzyme. According to another embodiment, the demethylating enzyme is a protein phosphatase 2A specific protein methylesterase. According to another embodiment, the therapeutically effective amount of the composition is from about 1 mg to about 10 g of the composition. According to another embodiment, the botanical raw material comprises at least one substance selected from the group consisting of gingko, allicin, bacopa; butcher's broom; flaxseed oil; a tacopherol; Vitamin E; ginseng, grape seed, St. John's wort; artichoke-powder; choline; inositol; tea; tobacco; and cocoa. According to another embodiment, the botanical raw material comprises a fruit of a species of plant genus *Coffea*. According to another embodiment, the fruit of the plant genus *Coffea* is a coffee bean. According to another embodiment, the botanical raw material comprises a ground or instant coffee. According to another embodiment, the botanical raw material comprises a nutritional supplement. According to another embodiment, the nutritional supplement comprises at least one tocopherol. According to another embodiment, the nutritional supplement comprises Vitamin E. According to another embodiment, the botanical raw material comprises a leaf of a tobacco plant. According to another embodiment, step (a) further comprises the step of extracting the botanical raw material with a polar solvent. According to another embodiment, the polar solvent is a lower alcohol. According to another embodiment, the polar solvent is ethyl acetate. According to another embodiment, step (a) further comprises the steps of solubilizing the methylation modifying compound in ethyl acetate below a pH of about 5 and partitioning the methylation modifying compound between an aqueous phase and ethyl acetate above a pH of about 10. According to another embodiment, the composition is essentially free of at least one substance selected from the group consisting of caffeine, caffeic acid and chlorogenic acid. According to another embodiment, in step (b) the composition is administered orally. According to another embodiment, the composition is a powder, a tablet, a capsule, a lozenge, or a suppository.

DETAILED DESCRIPTION OF THE INVENTION

Figure 1:
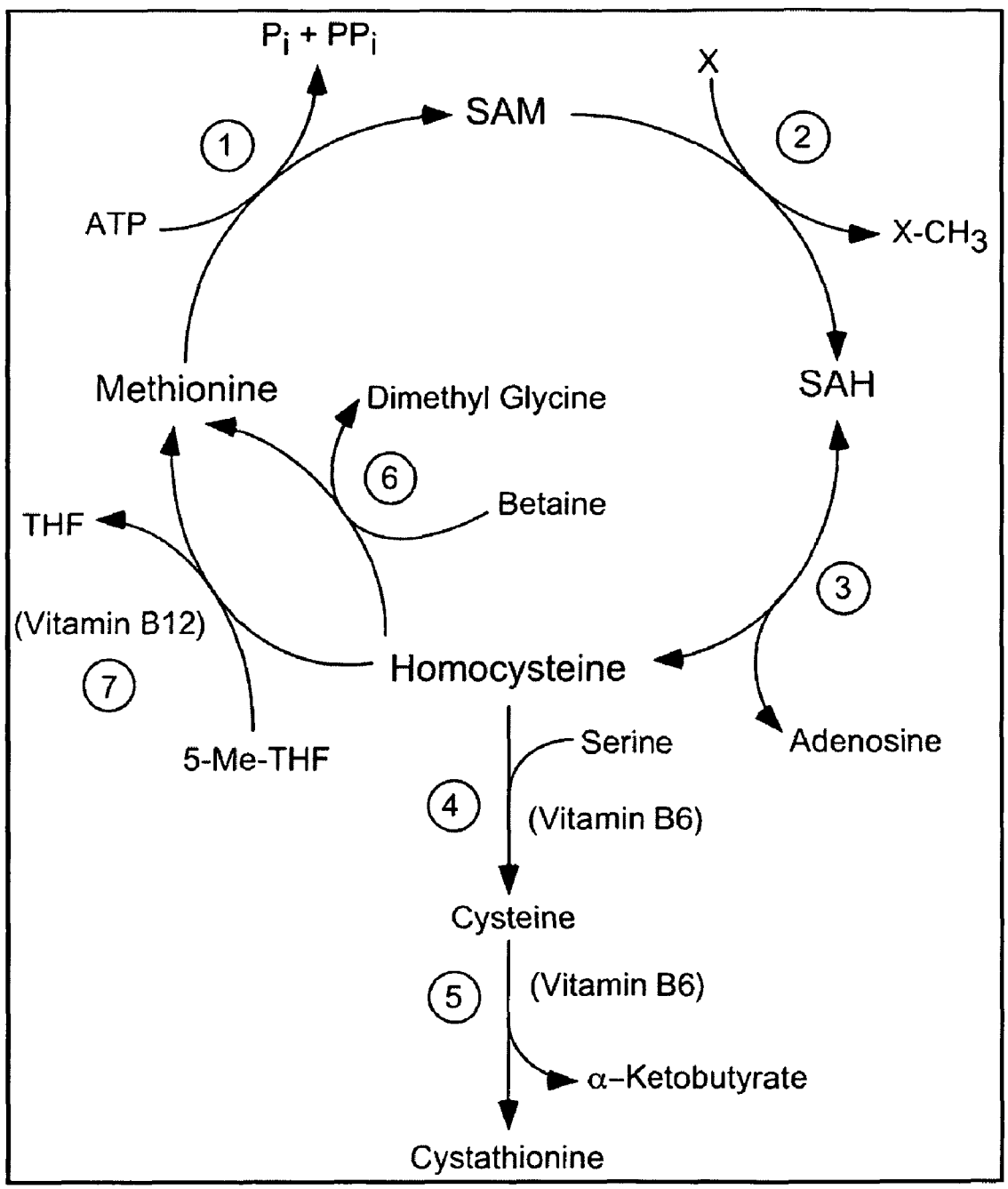
FIG. 1 provides a schematic diagram of the methyl cycle (1: methionine adenosyl transferase; 2: SAM-dependent methyl transferases; 3: SAH hydrolase; 4: Betaine homocysteine methyl transferases; 5: methionine synthase).
Figure 2:
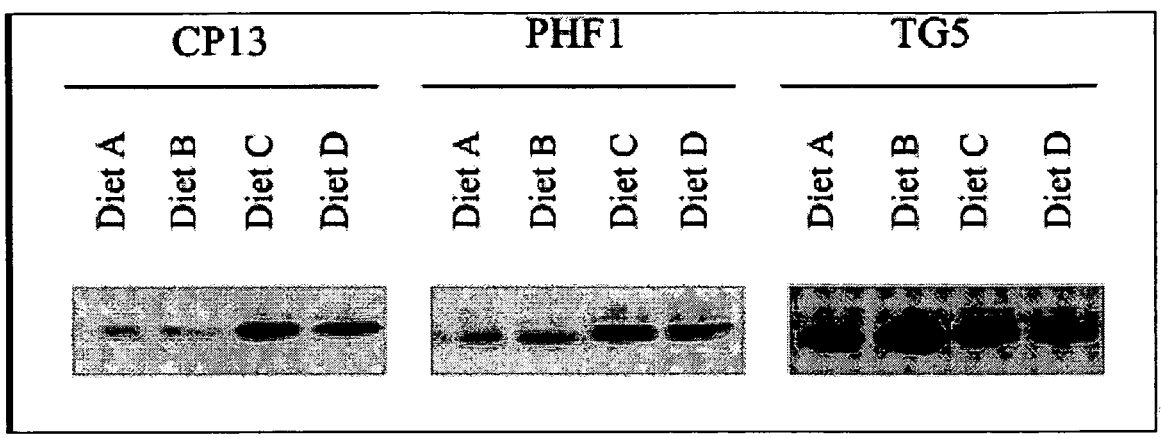
FIG. 2 provides Western blots after SDS-PAGE of extracts prepared from the brains of mice raised on normal diets (A and B) and vitamin-deficient diets (C and D).

The present invention encompasses novel compositions extracted from botanical and microbial extracts, methods of making the compositions, and methods of treating or preventing human disease using the novel compositions. The inventive extracts can dramatically decrease the demethylation of PP2A, thus increasing cognitive function and the resilience of cognitive function, particularly in persons suffering from or prone to developing Alzheimer's disease.

The present invention is based on the recognition that a botanical extract that stimulates methylation of PP2A or inhibits the demethylation of PP2A may be useful to treat certain health problems, including, but not limited to AD, that have been associated with decreases in PP2A methylation. It has long been believed that coffee products, in particular the caffeine in such products, aid in mental focus, learning, and memory. In one embodiment of the present invention, an extract of coffee that is essentially free of caffeine is shown to possess a botanical ingredient having PP2A-specific protein methylesterase inhibitor activity capable of enhancing cognitive function.

Definitions

The term "active constituent" is defined as the chemical constituent in a botanical raw material or a microbial raw material that is responsible for the intended therapeutic effect.

"Alkyl" as used herein refers to a straight or branched chain optionally substituted hydrocarbon having from one to 10 carbon atoms. Examples of "alkyl" as used herein include, but are not limited to methyl, ethyl, isopropyl n-butyl, t-butyl, and the like.

The term "botanical raw material" as used herein refers to a fresh or processed (e.g. cleaned, frozen, dried, sliced, dissolved, or liquefied) part of a single species of plant or a fresh or processed alga or macroscopic fungus.

The term "botanical ingredient" refers to a component that originates from a botanical raw material.

The term "botanical product" refers to a finished, labeled product that contains vegetable matter, which may include plant materials, algae, macroscopic fungi, or combinations thereof. Depending in part on its intended use, a botanical product may be a food, drug, medical device or cosmetic.

The term "botanical extract" as used herein refers to a product prepared by separating, by chemical or physical process, medicinally active portions of a plan from the inactive or inert components. The botanical extracts prepared according to the present invention preferably are obtained by means of a solvent, optionally under pressure and/or heat.

As used herein, the term "cognitive function" refers to the ability to perform mental tasks, such as thinking, learning, judging, remembering, computing, controlling motor functions, and the like. The expression "resilience of cognitive function" refers to the ability of functional elements of cognitive function to resist deterioration over time. As used herein, the term "cognitive function enhancing amount" refers to that amount of the composition of the present invention that will noticeably impact the ability to perform mental tasks, as measured by tests for memory, computation, attention, or other mental or cognitive attribute, or as suggested by an individual's perception of his or her abilities in these realms.

As used herein, the term "comestible" refers to a material that is suitable for human consumption, including a material that can be ingested by oral and by a non-oral means, e.g., an inhalant or a snuff. For purposes of the present invention, the term includes supplemented or enhanced foods.

The terms "dietary supplement" and "nutritional supplement" are used interchangeably herein to mean (1) a product intended to supplement the diet that bears or contains one or more of the following dietary ingredients: [A] a vitamin, [B] a mineral, [C] an herb or other botanical, [D] an amino acid, [E] a dietary substance for use by man to supplement the diet by increasing the total dietary intake; or (F) a concentrate, metabolite, constituent, extract, or combination of any ingredient described in clause (A), (B), (C), (D), or (E); and (2) a product that (A)(i) is intended for ingestion; (B) is not represented for use as a conventional food or as a sole item of a meal or the diet; and (C) is labeled as a dietary supplement. For purposes of the present invention, this definition includes tobacco.

The term "essentially free" means less than about 10% of the amount found in unprocessed material. For example, if a coffee bean contains about 1% w/w caffeine, then an extract that is essentially free of caffeine would contain less than about 0.1% caffeine w/w (excluding additional mass due to dilution in water).

The term "extracting" as used herein refers to the process of drawing out, withdrawing, distilling or otherwise separating one substance from another by a chemical or physical process.

The term "food" as used herein refers to (a) articles used for food or drink for man or other animals; (2) chewing gum; and (3) articles used for components of any such article.

The term "health" or "healthy" as used herein refers to a general condition of the body or mind with reference to soundness and vigor, as well as freedom from disease or ailment.

The term "lower alcohol" refers to a chemical compound of the general form R—OH, where R is an alkyl group having between one and six carbons.

As used herein, the phrase "methylation modifying compound" refers to an agent that either directly inhibits at least one enzyme that demethylates PP2A, including, but not limited to a PP2A-specific protein methylesterase, or that indirectly affects the methylation state of PP2A itself.

The term "microbe" or "microorganism" are used interchangeably herein to refer to an organism too small to be seen clearly with the naked eye, including, but not limited to, microscopic bacteria, fungi (molds), algae, protozoa, and viruses.

A "microbial raw material" as used herein refers to a fresh or processed (e.g. concentrated, frozen, dried, dissolved, liquefied, pelleted) part of a microbial culture.

The term "microbial ingredient" refers to a component that originates from a microbial raw material.

The term "microbial product" refers to a finished, labeled product that contains matter derived from a microbial culture.

The term "partitioning" as used herein refers to a process that takes advantage of the differential solubility of a substance in two solvents.

The terms "soluble" and "solubility" refer to the property of being susceptible to being dissolved in a specified fluid (solvent). The term "insoluble," as used herein refers to the property of a material that has minimal or limited solubility in a specified solvent.

The term "well-being" as used herein refers to a subject's physical and mental soundness.

Compositions of the Present Invention

One aspect of the present invention provides compositions comprising a methylation modifying compound isolated from a botanical raw material or microbial raw material (i) that inhibits at least one enzyme that demethylates PP2A, wherein the composition inhibits at least 50%, more preferably by at least 90%, of the demethylating activity of the demethylating enzyme as measured by levels of PP2A methyl esterification; or (ii) that stimulates the methylating activity of at least one enzyme that methylates PP2A. In a preferred embodiment, the methylation modifying compound comprises the portion of a botanical extract prepared from fruit of a species of the plant genus *Coffea* that is insoluble in ethyl acetate above a pH of about 10, yet that is soluble in ethyl acetate below a pH of about 5. Preferably, the composition is essentially free of caffeine, caffeic acid and/or chlorogenic acid. Caffeine, also known as trimethylzanthine, caffeine, theine, mateine, guaranine, methyltheobromine and 1,3,7-trimethylzanthine, is a xanthine alkaloid found naturally in coffee beans, tea, kola nuts, Yerba mate, guarana berries, and the like. Caffeic acid (3-(3,4-Dihydroxyphenyl)-2-propenoic acid), which is totally unrelated to caffeine, is found in many fruits, vegetables, seasonings and beverages consumed by humans, principally in conjugated forms such as chlorogenic acid. Chlorogenic acid, an ester of caffeic acid and quinic acid, is a major phenolic compound in coffee, isolated from the leaves and fruits of dicotyledonous plants. Chlorogenic acid also slows the release of glucose into the bloodstream after a meal. A skilled artisan will appreciate that if desired, caffeine and/or chlorogenic acid may be added to the composition.

In one embodiment, the composition of the invention is prepared by extracting coffee beans, the fruit of the coffee tree, either green, roasted or otherwise treated, of *C. arabica, C. robusta, C. liberica, C. arabusta*, or other species. The extraction procedure concentrates or isolates those agents in coffee that increase the methylation levels of PP2A. The composition of the invention includes extracts or compositions of coffee that are selected, isolated, bred, or genetically modified so as to increase the concentrations of the agents or classes of agents having these activities and includes compositions of coffee that are fortified with these agents extracted either from coffee or from other sources.

Our experiments with coffee extracts indicate that coffee contains agents that prevent the demethylation of PP2A by PPME and that these demethylation inhibitors are distinct from caffeine or its derivatives. Inhibition of this esterase results in an overall higher level of methyl-PP2A, and this would be expected to prevent tau hyperphosphorylation and tangle formation associated with AD. Our assay for this activity involves incubating the test compound with purified PPME and purified $^3$H-methyl-labeled PP2A in 50 mM MOPS buffer at pH 7.2. We have shown that extracts of several herbal substances have a significant inhibitory effect on PPME. We have analyzed a drip-brewed coffee embodiment of the present invention and extracts of coffee embodiments of the present invention in most detail (See Examples 4, 6, and 7). We have discovered that the inhibitor effect is due to a small molecule that is soluble in polar solvents and is not caffeine, chlorogenic acid or caffeic acid.

In another aspect, the present invention provides comestibles comprising a composition comprising a methylation modifying compound that inhibits at least one enzyme that demethylates PP2A, wherein the composition inhibits at least 50%, more preferably at least 90%, of the demethylating activity of the demethylating enzyme as measured by levels of PP2A methyl esterification, and wherein the methylation modifying compound is extracted from a botanical or microbial extract. Preferably the composition is extracted from fruit of a species of the plant genus *Coffea*. The comestibles of the invention include fruit-based drinks, coffee-based drinks, tea-based drinks, sport drinks, nutrition bars, snack foods, gums, cereals, candies, baby formulas, energy drinks, adult nutritional drinks, health drinks, and other food products. The term "sports drink" refers to a beverage that is supposed to rehydrate athletes, as well as restoring electrolytes, sugar and other nutrients, for example, Gatorade, POWERade, and All Sport. As used herein, the term "energy drink" refers to a beverage, including, but not limited to, Jolt Cola, Red Bull and similar products, that contains legal stimulants, vitamins and minerals; these products are formulated to give the user a burst of energy. The term "adult nutritional drink" as used herein refers to such products as Ensure, Longetics® or a similar product. The term "health drink" refers to any beverage purported to have beneficial health effects, including, but not limited to, reducing inflammation; supporting the immune system; neutralizing infectious agents; preventing clogged arteries, preserving cognitive function and inhibiting cancer growth. The comestible can comprise an additional ingredient that confers cognitive or other health benefits.

Yet another aspect of the invention provides pharmaceutical compositions comprising a composition comprising a methylation modifying compound that inhibits at least one enzyme that demethylates PP2A, wherein the composition inhibits at least 50%, more preferably at least 90%, of the demethylating activity of the demethylating enzyme as measured by levels of PP2A methyl esterification, and wherein the methylation modifying compound is extracted from a botanical or microbial extract. Preferably, the composition is extracted from fruit of a species of the plant genus *Coffea*. The pharmaceutical composition can be formulated for oral consumption or in the form of a suppository. The pharmaceutical compositions of the invention include powders, tablets, capsules and lozenges.

Another aspect of the invention provides methods of enhancing cognitive function in a human, the method comprising the step of administering a cognitive function enhancing amount of a composition comprising a methylation modifying compound that inhibits at least one enzyme that demethylates PP2A, wherein the composition inhibits at least 50% of the demethylating activity of the demethylating enzyme as measured by levels of PP2A methyl esterification, and wherein the methylation modifying compound is extracted from a botanical or microbial extract. Preferably the composition is extracted from fruit of a species of the plant genus *Coffea*. Alternatively, a method of enhancing cognitive function in a human according to the present invention comprising the step of administering a comestible comprising a cognitive function enhancing amount of a composition comprising a methylation modifying compound that inhibits at least one enzyme that demethylates PP2A, wherein the composition inhibits at least 50% of the demethylating activity of the demethylating enzyme as measured by levels of PP2A methyl esterification, and wherein the methylation modifying compound is extracted from a botanical or microbial extract.

The invention also provides methods of enhancing memory in a human, which method comprises administering a memory enhancing amount of a composition or a comestible comprising methods of enhancing cognitive function in a human, the method comprising the step of administering a cognitive function enhancing amount of a composition comprising a methylation modifying compound that inhibits at least one enzyme that demethylates PP2A, wherein the composition inhibits at least 50% of the demethylating activity of the demethylating enzyme as measured by levels of PP2A methyl esterification, and wherein the methylation modifying compound is extracted from either a botanical or a microbial extract. According to the present invention, the composition can be used in methods of treating or preventing any disease, condition or disorder where defects in methylation metabolism appear to play a role as evidenced by an association of the disease, condition or disorder with plasma homocysteine levels that are elevated relative to normal plasma homocysteine levels. Such diseases, conditions or disorders include, but are not limited to, neurodegenerative diseases, disorders or conditions, such as Parkinson's disease, neuropsychiatric diseases, disorders or conditions, such as bipolar disorder, Alzheimer's disease, heart disease, arthritis, diabetes and certain cancers. The term "neurodegenerative" as used herein refers to a disease, condition or disorder marked by the loss or diminution of an original nerve cell function, and the term "neuropsychiatric" relates to organic and functional diseases, conditions or disorders of the nervous system.

Yet another aspect of the invention provides processes for preparing a composition comprising a methylation modifying compound that inhibits at least one enzyme that demethylates PP2A, wherein the composition inhibits at least 50%, more preferably at least 90%, of the demethylating activity of the demethylating enzyme as measured by levels of PP2A methyl esterification, and wherein the methylation modifying compound is extracted from either a botanical extract or a microbial extract. When the composition of the present invention is extracted from the fruit of a species of the plant genus *Coffea*, the process of the present invention comprises the steps: determining when the composition inhibits at least 50%, more preferably at least 90%, of the demethylating activity of the demethylating enzyme as measured by levels of PP2A methyl esterification, and optionally treating the fruit to remove caffeine. The extract can be treated further to remove chlorogenic acid and/or caffeic acid.

Methods of Preparing Compositions of the Invention

Another aspect of the invention provides a method of preparing a concentrated purified extract comprising a composition useful for enhancing or maintaining cognitive health. One method of preparing a composition of the invention is to extract the active agents from botanical raw material or microbial raw material into organic solvents from aqueous solutions at acid or neutral pH. Further concentration of the agents can be effected by extracting them from organic solvents back into aqueous solvents at basic pH. In one preferred embodiment involving a botanical raw material, the method comprises the steps: (a) contacting the fruit of a species of plant with a polar organic solvent for a time sufficient to form an extract solution, b) removing particulate matter from the extract solution; (c) isolating the extract solution and removing the polar organic solvent to form a concentrated primary extract, (d) washing the concentrated primary extract with a solvent in which impurities are soluble and the agent is poorly soluble; (e) removing the solvent; and (f) dissolving the desired methylation modifying agent in a polar organic solvent or in water at neutral to basic pH. For example, a coffee extract is prepared by:

a) contacting a species of the fruit of a species *Coffea* with pure ethanol at an elevated temperature (80 C) for about 5-10 minutes, i.e., a time sufficient to form an ethanol extract solution from the fruit.

b) removing particulate matter from the ethanol extract solution by filtration or centrifugation;

c) isolating the ethanol extract solution and removing the ethanol by evaporation in a glass flask to form a concentrated primary extract;

d) washing the concentrated extract with deionized water at a pH below about 5;

e) drying the extract to remove residual water; and f) dissolving the extract in ethanol to form a washed concentrated primary extract.

The term "solvent" as used herein refers to a substance, usually liquid, capable of dissolving or dispersing one or more other substances. Chemists have classified solvents into two broad categories according to their polarity: polar and nonpolar. A common measure of the polarity of a solvent is the dielectric constant. The term "polar solvent" as used herein refers to a compound that is composed of polar molecules. A "polar molecule" is one in which there is some separation of charge in the chemical bonds, so that one part of the molecule has a slight positive charge and the other a slight negative charge. Polar solvents may be further classified as protic or aprotic. The term "protic" refers to a hydrogen atom attached to an electronegative atom, while the term "aprotic" refers to a molecule that does not contain an O—H bond. A "polar protic solvent" can be represented by the general formula ROH; the polarity of the polar protic solvent stems from the bond dipole of the O—H bond. Examples of polar protic solvents include, but are not limited to, water, alcohols, and acetic acid. A "dipolar aprotic solvent" is one that contains a bond that has a large bond dipole. Typically, this bond is a multiple bond between carbon and either oxygen or nitrogen. Most dipolar aprotic solvents contain a C—O double bond. Examples of dipolar aprotic solvents include, but are not limited to, acetone and ethyl acetate. As the number of —CH$_2$— groups in ROH increases, and the relative amount of hydrocarbon character increases, the polarity decreases. The term "nonpolar solvent" refers to compounds that have low dielectric constants and are not miscible with water. Examples of nonpolar solvents include, but are not limited to benzene, carbon tetrachloride, and diethyl ether.

Optionally, the washed concentrated primary extract can be dissolved in water and the pH of the washed concentrated primary extract neutralized. The extract then can be further purified by utilizing the property that the desired agent is insoluble in ethyl acetate above a pH of about 10.0, and is soluble in ethyl acetate below a pH of about 5.0. It would be apparent to a skilled artisan that by assaying for the desired effects on PP2A methylation (see PCT/US03/07658; the contents of which are incorporated by reference) one can readily identify growth conditions and plant varieties having increased levels of the agents of the compositions of the present invention. Likewise, using methods known in the art, a skilled artisan could genetically engineer or breed plant varietals to express increased amounts of the desired agents.

The compositions of the present invention may be in a form suitable for oral use, for example, as tablets, troches, lozenges, aqueous or oily suspensions, solutions, dispersible powders or granules, emulsions, hard or soft capsules, syrups or elixirs, pastes, gels or the like. Compositions intended for oral use may be prepared according to any known method, and such compositions may contain one or more agents selected from the group consisting of sweetening agents, flavoring agents, coloring agents, and preserving agents in order to provide pharmaceutically elegant and palatable compositions. Tablets may contain the active ingredient(s) in admixture with non-toxic pharmaceutically-acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They also may be coated for controlled delivery. For example, a "delayed release" dosage form releases a product or substance at a time other than promptly after administration. Examples of delayed-release systems include repeat-action tablets and capsules, and enteric-coated tablets where timed release is achieved by a barrier coating.

Compositions of the present invention also may be formulated for oral use as hard gelatin capsules, where the active ingredient(s) is(are) mixed with an inert solid diluent, for example, calcium carbonate, calcium phosphate or kaolin, or soft gelatin capsules wherein the active ingredient(s) is (are) mixed with water or an oil medium, for example, peanut oil, liquid paraffin, or olive oil.

The compositions of the present invention may be formulated as aqueous suspensions wherein the active ingredient(s) is (are) in admixture with excipients suitable for the manufacture of aqueous suspensions. Such excipients are suspending agents, for example, sodium carboxymethylcellulose, methylcellulose, hydroxy-propylmethylcellulose, sodium alginate, polyvinylpyrrolidone, gum tragacanth, and gum acacia; dispersing or wetting agents may be a naturally-occurring phosphatide such as lecithin, or condensation products of an alkylene oxide with fatty acids, for example, polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions also may contain one or more coloring agents, one or more flavoring agents, and one or more sweetening agents, such as sucrose or saccharin.

Compositions of the present invention may be formulated as oily suspensions by suspending the active ingredient in a vegetable oil, for example arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral composition. These compositions may be preserved by the addition of an antioxidant such as ascorbic acid.

Compositions of the present invention may be formulated in the form of dispersible powders and granules suitable for composition of an aqueous suspension by the addition of water. The active ingredient in such powders and granules is provided in admixture with a dispersing or wetting agent, suspending agent, and one or more preservatives. Suitable dispersing or wetting agents and suspending agents are exemplified by those already mentioned above. Additional excipients, or example, sweetening, flavoring and coloring agents also may be present.

The compositions of the invention also may be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate. The emulsions also may contain sweetening and flavoring agents.

The compositions of the invention also may be formulated as syrups and elixirs. Syrups and elixirs may be formulated with sweetening agents, for example, glycerol, propylene glycol, sorbitol or sucrose. Such formulations also may contain a demulcent, a preservative, and flavoring and coloring agents. Demulcents are protective agents employed primarily to alleviate irritation, particularly mucous membranes or abraded tissues. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

The compositions of the present invention also may be in the form of a sterile injectable aqueous or oleaginous suspension. Injectable compositions, such as sterile injectable aqueous or oleaginous suspensions, may be formulated according to the known art using suitable dispersing or wetting agents and suspending agents. The sterile injectable composition may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For parenteral application, "parenteral" meaning subcutaneous injections, intravenous, intramuscular, intrasternal injection, or infusion techniques, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The terms "drug carrier", "carrier", or "vehicle" are used interchangeably to refer to carrier materials suitable for administration of the methylation modifying compounds. Carriers and vehicles useful herein include any such materials known in the art which are nontoxic and do not interact with other components. As used herein the term "a pharmaceutically acceptable carrier" refers to any substantially non-toxic carrier conventionally useable for administration in which the compound will remain stable and bioavailable.

The compositions of the present invention may be in the form of suppositories for rectal administration of the composition. These compositions can be prepared by mixing the active ingredient with a suitable nonirritating excipient such as cocoa butter and polyethylene glycols which are solid at ordinary temperatures but liquid at the rectal temperature and will therefore melt in the rectum and release the drug. When formulated as a suppository the compositions of the invention may be formulated with traditional binders and carriers, such as triglycerides.

Compositions of the present invention optionally can include an excipient. The term "excipients" as used herein refers to pharmaceutically acceptable organic or inorganic carrier substances which do not deleteriously react with the active compounds. Suitable dietary excipients include, but are not limited to, dietary suitable starch, vegetable oil, vegetable gums, gelatins, soy extracts, sugars, grains, natural and artificial flavorings, and the like. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil; fatty acid monoglycerides and diglycerides, petroethral fatty acid esters, hydroxymethylcellulose, polyvinylpyrrolidone, and the like. Suitable excipients are described in detail in Remington's Pharmaceutical Sciences, Twentieth Edition, © 2000 incorporated herein by reference.

Pharmaceutical compositions can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds.

The therapeutically active agent of the present invention can be formulated per se or in salt form. The term "pharmaceutically acceptable salts" refers to nontoxic salts of the active agent. Pharmaceutically acceptable salts include, but are not limited to, those formed with free amino groups such as those derived from hydrochloric, phosphoric, sulfuric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, and the like.

Additional compositions of the present invention can be readily prepared using technology which is known in the art such as described in Remington's Pharmaceutical Sciences.

A composition of the present invention, alone or in combination with other active ingredients, may be administered to a subject in a single dose or multiple doses over a period of time, generally by oral administration. As used herein, the terms "therapeutically effective amount," "memory-enhancing amount", and "cognition enhancing amount" are used interchangeably to refer to the amount of the composition of the invention that results in a therapeutic or beneficial effect, including a subject's perception of health or general well-being, following its administration to a subject.

It is believed that an increase in the level of PP2A methylation will bring about the protection or enhancement of cognitive functioning, or preventing a cognitive disorder from manifesting or deepening. Thus the therapeutic effect of the compositions of the present invention can exert a protective or enhancing effect on cognitive function; minimize, prevent or ameliorate cognitive symptoms of a disease or disorder, or may have any other beneficial effect.

The concentration of the substance is selected so as to exert its therapeutic effect, but low enough to avoid significant side effects within the scope and sound judgment of the skilled artisan. The effective amount of the composition may vary with the age and physical condition of the biological subject being treated, the severity of the condition, the duration of the treatment, the nature of concurrent therapy, the specific compound, composition or other active ingredient employed, the particular carrier utilized, and like factors. Those of skill in the art can readily evaluate such factors and, based on this information, determine the particular effective concentration of a composition of the present invention to be used for an intended purpose.

A skilled artisan can determine a therapeutically effective amount of the inventive compositions by determining the unit dose. As used herein, a "unit dose" refers to the amount of inventive composition required to produce a response of 50% of maximal effect (i.e. $ED_{50}$). The unit dose can be assessed by extrapolating from dose-response curves derived from in vitro or animal model test systems. The amount of compounds in the compositions of the present invention which will be effective in the treatment of a particular disorder or condition will depend on the nature of the disorder or condition, and can be determined by standard clinical techniques. (See, for example, Goodman and Gilman's THE PHARMACOLOGICAL BASIS OF THERAPEUTICS, Joel G. Harman, Lee E. Limbird, Eds.; McGraw Hill, New York, 2001; THE PHYSICIAN'S DESK REFERENCE, Medical Economics Company, Inc., Oradell, N.J., 1995; and DRUG FACTS AND COMPARISONS, FACTS AND COMPARISONS, INC., St. Louis, Mo., 1993). The precise dose to be employed in the formulation will also depend on the route of administration, and the seriousness of the disease or disorder, and should be decided according to the judgment of the practitioner and each patient's circumstances. Various administration patterns will be apparent to those skilled in the art.

The dosage ranges for the administration of the compositions of the present invention are those large enough to produce the desired therapeutic effect. Preferably, the cognitive function enhancing amount of the compositions of the present invention is administered one or more times per day on a regular basis. A typical dose administered to a human is between about 1 mg and about 10 g of the composition, preferably between 1 mg and 1 g of the composition.

Those skilled in the art will recognize that initial indications of the appropriate therapeutic dosage of the compositions of the invention can be determined in in vitro and in vivo animal model systems, and in human clinical trials. One of skill in the art would know to use animal studies and human experience to identify a dosage that can safely be administered without generating toxicity or other side effects. For acute treatment where it is desirable to substantially increase methylated PP2A, it is preferred that the therapeutic dosage be close to the maximum tolerated dose. For chronic preventive use, lower dosages may be desirable because of concerns about long term effects. However, coffee and coffee extracts are commonly believed to be safe and have a history of human use. The composition preferably is administered one or more times per day, in food or beverage, as inhalant, in a gum, transdermally, as a suppository, or as a snuff. As used herein, the term "inhalants" refers to substances or combinations of substances that, by virtue of their high vapor pressure, can be carried by an air current into the nasal passage where they exert their effect. The container from which the inhalant is administered is "an inhaler."

Alternatively, the composition of the present invention may be administered at least once per day in combination with a prescribed drug. For example, the composition of the present invention may be administered together with existing anti-cholinesterase drugs now prescribed for Alzheimer's, with various anti-inflammatory agents, or with statins.

In another aspect, the composition of the present invention is administered at least once per day in combination with a dietary or nutritional supplement believed to have beneficial health effects. For example, Coenzyme $Q_{10}$ (also known as $CoQ_{10}$, $Q_{10}$, vitamin $Q_{10}$, ubiquinone and ubidecarenone), a benzoquinone compound synthesized naturally by the human body, is used by cells of the body in oxidative metabolism or cell respiration and as an endogenous antioxidant. An "antioxidant" is a substance that protects cells from free radicals, which are highly reactive chemicals often containing oxygen atoms, that are capable of damaging important cellular components, such as DNA and lipids. The plasma level of $CoQ_{10}$ has been used in studies as a measure of oxidative stress, a situation in which normal antioxidant levels are reduced. Various investigations have explored the usefulness of $CoQ_{10}$ as a treatment for diseases, including, but not limited to, cancer and cardiovascular disease.

Idebenone, a synthetic analog of $CoQ_{10}$, has been investigated in elderly patients with dementia. Studies suggest that it may diminish nerve cell damage due to ischemia and facilitate memory and learning.

Huperzine A, a natural acetylcholinesterase inhibitor derived from the Chinese herb *Huperzia serrata*, has antioxidant and neuroprotective properties, and has been proposed as a disease-modifying treatment for AD.

Galantamine, an acetylcholinesterase inhibitor, is used to treat symptoms of AD.

Vincamine and vinpocetine, a semisynthetic derivative of vincamine, an alkaloid derived from the plant Vina minor L, are used in Europe, Japan and Mexico as pharmaceutical agents for the treatment of cerebrovascular and cognitive disorders.

Acetyl-L-carinitine, an acetylated derivative of carnitine, has been shown to promote fatty acid beta-oxidation in liver and to prevent motor nerve condition velocity slowing in diabetic rats.

Dehydroepiandrosterone (DHEA), a steroid, is being studied in the prevention of cancer. In the body, it is a precursor produced by the adrenal gland and converted to testosterone or the estrogens.

Phosphatidylcholine, a phospholipid that is a major component of cell membranes, has putative activity as a cognition enhancer and in cell-membrane repair Gingko, an herb, has putative properties as a neuroprotective agent, an antioxidant, a free-radical scavenger, a membrane stabilizer, and an inhibitor of platelet-activating factor. Sherpina, V. S., et al., *American Family Physician* 68(5) 923-926 (2003). Gingko extract also has been shown to inhibit beta-amyloid deposition. Id.

Circumin, an active ingredient in turmeric, which is in curry, purportedly has anti-inflammatory and cholesterol lowering properties.

Ginseng, a Chinese herb, has been used for centuries in Asia as a cure for many maladies.

Research has shown that Vitamin E (DL-alpha-tocopherol), an essential vitamin that functions as an antioxidant, can help prevent cardiovascular disease and increase the immune response. It has been hypothesized that Vitamin E and its analogs and derivatives may prevent brain cell damage by destroying toxic free radicals. The term "tocol" generally refers to 2-methyl-2-(4,8,12-trimetyltridecyl)chroman-6-ol; the term "tocopherol" generally refers to all mono, di, and trimethyltocols, including, but not limited to, alpha-tocopherol (5,7,8-trimethyltocol), beta-tocopherol (5,8-dimethyltocol), gamma-tocopherol (7,8-dimethyltocol), delta-tocopherol (8-methyltocol), the term "tocotrienol" refers to 2-methyl-2-(4,8,12-trimethyltrideca-3,7,11-trienyl)chroman-6-ol; and the term "vitamin E" generally refers to all tocol and tocotrienol derivatives exhibiting qualitatively the biological activity of alpha-tocopherol.

It is well-known that N-acetyl-cysteine (NAC) promotes cellular glutathione production, and thus reduces, or even prevents, oxidant mediated damage. Treatment with NAC provides beneficial effects in a number of respiratory, cardiovascular, endocrine, infectious, and other disease settings.

B vitamins, such as folic acid, are known to reduce levels of homocysteine, an amino acid already linked, at high levels, to an increased risk of heart attacks, strokes and Alzheimer's disease.

Lecithin, a lipid material composed of choline and inositol, is a major component of cell membranes. As used by producers of lecithin for commercial use, the term "lecithin" refers to a complex mix of phosphatides and other substances that contain phosphatidylcholine.

Choline (trimethyl ethanolamine), a quaternary saturated amine classified as an essential nutrient by the Food and Nutrition Board of the Institute of Medicine, is a component of lecithin. Choline is needed by the body to make the neurotransmitter acetylcholine.

Fish oil, which is oil derived from the tissues of oily fish, naturally contains the omega-3 fatty acids eicosapentaenoic acid (EPA) and docosahexaenoic acid (DHA). Some experts believe that fish oil can help regulate cholesterol in the body. It also may help protect the brain from cognitive problems associated with Alzheimer's disease.

Deprenyl (selegiline, Eldepryl®), a monoamine oxidase inhibitor, is prescribed for the treatment of early-stage Parkinson's disease and senile dementia.

The compositions of the invention can be used alone or in combination with other pharmaceuticals or herbals to prolong mental health, to maintain or enhance cognitive functioning or memory, or to preserve mental or physical well-being and health. The compositions can also be used to prevent or treat effects a number of ailments, including, but not limited to, Alzheimer's disease; Parkinson's disease; heart disease; arthritis; age-related degeneration, functional impairments, and diseases; diabetes, and cancer, have on cognitive function.

The effectiveness of the compositions and methods of the present invention can be assayed by a variety of protocols. The effects of increasing cognitive function in a human subject can be determined by methods routine to those skilled in the art including, but not limited to, both paper and pencil, and computer tests. One of skill in the art can also directly measure PP2A methylation levels, tau protein phosphorylation levels, neurofibrillary tangle formation and neurodegeneration in animal models.

Comestibles of the Invention

Compositions of the present invention may be included in a variety of forms, including, but not limited to, nutritional supplements, pharmaceutical compositions, vitamin supplements, food additives or foods supplements. For example, the methylation modifying compounds described may be embodied as a lozenge, candy, drink, gum, or other snack, food, pill, snuff, nutritional or food supplement, or delivered as an ingredient of an inhalant, beverage, or transdermal delivery system. For example, the methylation modifying compounds of the present invention may be added directly to a liquid beverage, such as water.

The compositions of the present invention may be in the form of a dispersible dry powder for pulmonary delivery. Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. The composition of the present invention is placed within a suitable dosage receptacle in an amount sufficient to provide a subject with a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. Nos. 4,227,522; 4,192,309; and 4,105,027. Suitable containers also include those used in conjunction with Glaxo's Ventolin® Rotohaler brand powder inhaler or Fison's Spinhaler® brand powder inhaler. Another suitable unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). All of these references are incorporated herein by reference.

The terms "transdermal delivery system", "transdermal patch", or "patch" refer to an adhesive system placed on the skin to deliver a time released dose of a drug(s) by passage from the dosage form through the skin to be available for distribution via the systemic circulation. Transdermal patches are a well-accepted technology used to deliver a wide variety of pharmaceuticals, including, but not limited to, scopolamine for motion sickness, nitroglycerin for treatment of angina pectoris, clonidine for hypertension, estradiol for post-menopausal indications, and nicotine for smoking cessation. Patches suitable for use in the present invention include, but are not limited to, (1) the matrix patch; (2) the reservoir patch; (3) the multi-laminate drug-in-adhesive patch; and (4) the monolithic drug-in-adhesive patch; TRANSDERMAL AND TOPICAL DRUG DELIVERY SYSTEMS, pp. 249-297 (Tapash K. Ghosh et al. eds., 1997), hereby incorporated herein by reference. These patches are well known in the art and generally available commercially.

In preferred embodiments, the comestibles of the invention include a coffee without caffeine, a decaffeinated coffee, a coffee-like beverage, a ready-to-drink coffee, a coffee dessert or any other coffee product enriched for, or selected for, PP2A methylation activity and used for the health functions described above.

When provided to non-human mammalian subjects, the compositions of the present invention may be administered separately or may be combined with ordinary feed or liquid nourishment to effect the alterations in body composition as described herein.

The compositions of the invention can be combined with ordinary foods to enhance the value of the palatability of the composition. For example, the compositions can be mixed with soft drinks, food supplements, candy, or high-energy bars, and virtually any other food that can be supplemented with a powder or liquid. Thus, the invention specifically includes food substances of specific types combined with the composition of the invention in specified forms and quantities.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Composition of Pure PP2A Methyltransferase

This example provides a method of preparing pure PPMT for use in assays of demethylation of PP2A. PPMT was obtained using a bacterial overexpression system consisting of the pMT and pBADESL plasmids in *Escherichia coli* strain C41(DE3) (obtained from S. Djordjevic, University College London) (George, R. R. et al., *Protein Expr. Purif.* 26(2): 266-74 (2002). LB flasks containing 0.2% (w/v) arabinose were inoculated and grown at 37° C. to a density of $A_{600}$=0.5. 1 mM isopropyl-b-D-thiogalactoside (IPTG), an artificial inducer of the Lac operon, was added to induce methyltransferase expression and after 3 hr the culture was centrifuged and the pellet washed with 0.1 M potassium phosphate, pH 7. The pellet was resuspended in 50 mM Tris, pH 7, containing 300 mM NaCl, 10% (v/v) glycerol, 10 mM 2-mercaptoethanol, sonicated on an ice/NaCl bath, and centrifuged. The supernatant was loaded on a pre-equilibrated 10 ml Ni-NTA superflow column, and eluted with a 150 ml gradient from 0 to 300 mM imidazole. The methyltransferase containing fractions were collected, pooled, concentrated and loaded onto a Sephacryl S-100 gel filtration column, eluted, and fractions collected. The presence of PPMT in the fractions was confirmed by SDS-PAGE analysis. Relevant fractions were pooled and loaded onto a pre-equilibrated Toyopearl Super-Q 650S column. The column then was washed, and the proteins eluted with a gradient of 0 to 500 mM NaCl. Fractions containing pure PPMT were pooled, dialyzed against 50 mM 4-morpholinepropanesulfonic acid, 3-(N-Morpholino)-propanesulfonic acid (MOPS) buffer containing 10% (v/v) glycerol, 1 mM dithiothreitol (DTT), 1 mM ethylenediaminetetraacetic acid (EDTA), and stored at −20° C. with 40% glycerol. The protocol yielded approximately 10 mg of pure PPMT per liter of culture media.

Example 2

Pure PP2A Methylesterase

This example provides a method of preparing pure PPME for use in assays of PP2A methyl esterification. A PP2A methylesterase plasmid (obtained from S. Djordjevic, University College London) was transformed into *E. coli* strain BL21(DE3) cells. LB flasks were inoculated with cultures grown overnight and allowed to grow at 37° C. When the culture reached a density of $A_{600}$=0.5. 1 mM IPTG was added to induce esterase expression. After 3 hr the cultures were centrifuged and the pellet was washed with 0.1 M potassium phosphate, pH 7, and resuspended in 50 mM Tris buffer containing 300 mM NaCl, 10% glycerol, 10 mM 2-mercaptoethanol. Cells were then disrupted by sonication and the supernatant was loaded on a pre-equilibrated 10 ml Ni: NTA superflow column. The column was washed with Tris-buffer and proteins were eluted with a 150 ml gradient from 0 to 300 mM imidazole. The methylesterase containing fractions were collected, pooled and dialyzed against 50 mM Tris buffer containing 5% (w/v) glycerol and 1 mM DTT. The proteins were then loaded onto a pre-equilibrated Toyopearl Super-Q 650S column. The column was washed and proteins collected by applying a gradient from 0 to 500 mM NaCl. Fractions containing pure PPME were pooled, dialyzed against 50 mM MOPS buffer containing 10% (v/v) glycerol, 1 mM DTT, 1 mM EDTA and stored at −20° C. with 40% glycerol. This protocol gives approximately 10 mg of pure PPME per liter of culture media.

Example 3

Purification of PP2A AC Dimers

This example provides a method of preparing pure PP2A AC dimers for use in assays of PP2A methyl esterification. (Lee, J., Stock, J., J. Biol. Chem. 268 (26) 19192-195 (1993); Tolstykh, T. et al., *EMBO J.* 19 (21): 5682-91 (2000)). Two frozen bovine brains were suspended into 800 ml of Buffer A (20 mM MOPS-Na, pH 7.2, 1.0 mM EDTA/DTT and 0.5 mg/L of aprotinin, leupeptin and pepstatin ("protease inhibitors"), and blended until smooth at 4 C. 25% $(NH_4)_2SO_4$ was added to the brains, stirred for 30 min and centrifuged. $(NH_4)_2SO_4$ was added to the supernatant to 70%, stirred for 60 min, and centrifuged. The precipitate in the pellet was collected and dissolved in 200 ml Buffer A and then dialyzed at 4 C against three, 4 liter changes of Buffer A. The dialyzed solution was clarified by centrifugation and the supernatant was loaded onto a DEAE-Toyopearl 650M column pre-equilibrated with Buffer A. The column was washed and PP2A eluted with Buffer A+0.3 M NaCl. The eluted PP2A was concentrated in 60 ml Buffer B (50 mM MOPS, pH 7.2, 1 mM EDTA/DTT, 0.5 mg/ml protease inhibitors) with 0.8M $(NH_4)_2SO_4$, loaded onto a TSK phenyl column and washed in this buffer before elution with a 1.0 L linear gradient from 0.8M $(NH_4)_2SO_4$ to 20% ethylene glycol in Buffer B. Fractions with phosphatase activity were collected and concentrated with a Centriprep concentrator before being loaded on a Sephacryl S-200 column pre-equilibrated in Buffer B with 0.2M NaCl. Fractions with phosphatase activity were pooled, buffer exchanged, and concentrated to 2 ml in Buffer C (50 mM MOPS, pH 7.2, 1 mM EDTA, 1 mM DTT) using a Centriprep concentrator. Concentrated protein was loaded on a Source-15Q HPLC column. A gradient from 0.2M to 0.35 M NaCl in Buffer C in 30 minutes, then from 0.35 M NaCl to 0.5 M NaCl in Buffer C in 10 minutes was used to elute the PP2A. Fractions containing the pure PP2A were collected, concentrated using a Centriprep concentrator, and stored at −20° C. with 40% glycerol.

Example 4

Assay for Methylesterase Inhibition

This example provides a method by which the rate of demethylation of methyl PP2A can be determined. For the composition of $^3$H-labeled methyl-PP2A, 100 μl reaction mixtures consisting of purified PP2A AC dimers (prepared as described in Example 3), purified PPMT (prepared as described in Example 1), 50 mM MOPS buffer pH 7.2, 5 mM DTT, 1 mM EDTA, 1 mg/ml BSA and 10 μl 3H-SAM were incubated at 37° C. for 30 min and loaded onto a desalting column pre-equilibrated in 50 mM MOPS-Na pH 7.2, 1 mM DTT, 1 mM EDTA, 200 mM NaCl and 5% glycerol. The sample was eluted with the same buffer, 50 μl fractions were collected, and each aliquot analyzed by scintillation counting. Fractions containing $^3$H-methyl PP2A were collected and stored at 4° C.

The following assay (see Lee, J. et al., Proc. Nat'l Acad. Sci. U.S.A. 93(12): 603-47 (1996)) is referred to subsequently as the "filter paper method". The test compound was incubated with purified PPME (prepared as described in Example 2) and purified $^3$H-methyl-labeled PP2A (the preparation of which is described in the preceding paragraph) in Buffer C (50 mM MOPS, 1 mM EDTA, 1 mM DTT buffer at pH 7.2, as in Example 3). After incubation at 37° C. for a fixed time (typically 10 minutes), the reaction mixture was spotted onto a 1 cm$^2$ piece of Whatman 3MM filter paper. The filter paper was immediately dipped in 10% ice-cold TCA, and then kept on ice in a plastic tray. After all reactions were run, the filter papers were washed at 4 C with stirring in a large excess of 10% TCA, similarly washed twice at 4 C with 100% methanol, and then vacuum dried at 45° C. for 1 hr to remove the $^3$H-methanol produced by PP2A demethylation. The dried filter papers then were assayed for radioactivity by submerging them in scintillation fluid and performing scintillation counting. This procedure is easily adapted to a 96-well format to allow high-throughput screening (described below).

As used herein to refer to assay results, the term "inhibition activity" refers to the following relationship:

$$\text{Inhibition activity} = 1 - \frac{\left(\begin{array}{c}\text{amount of methyl-}\\ \text{PP2A demethylated with inhibitor}\end{array}\right)}{\left(\begin{array}{c}\text{amount of methyl-}\\ \text{PP2A demethylated without inhibitor}\end{array}\right)}$$

The activity of an inhibitor according to the present invention is defined herein as 1 unit of inhibitor inhibits 50% of the demethylation in 10 μl of reaction mixture in 10 minutes.

Drip-brewed coffee (prepared from Sumatra coffee purchased from Starbucks Coffee) was tested in an initial screen. The filter paper assay described above was used to assay 1 μl of Sumatra coffee per 10 μl of assay mixture. The assay showed that Sumatra coffee contained an inhibition activity of 0.83 (i.e., 83% inhibition relative to control).

Based on this significant inhibition of PPME, we tested an ethanol extract of Sumatra coffee that showed an even more significant inhibitory effect. 10 g of ground Sumatra coffee bean (Starbucks) was extracted in ethanol at 80° C. for 5 minutes with stirring. After cooling, the extract was filtered through a Whatman No. 54 paper filter. The filtered extract was rotary evaporated at 40° C. until the volume was reduced to approximately 1 ml. The liquid phase was recovered and diluted into 50 mM MOPS buffer, 1 mM EDTA, pH 7.2.

Figure 3:
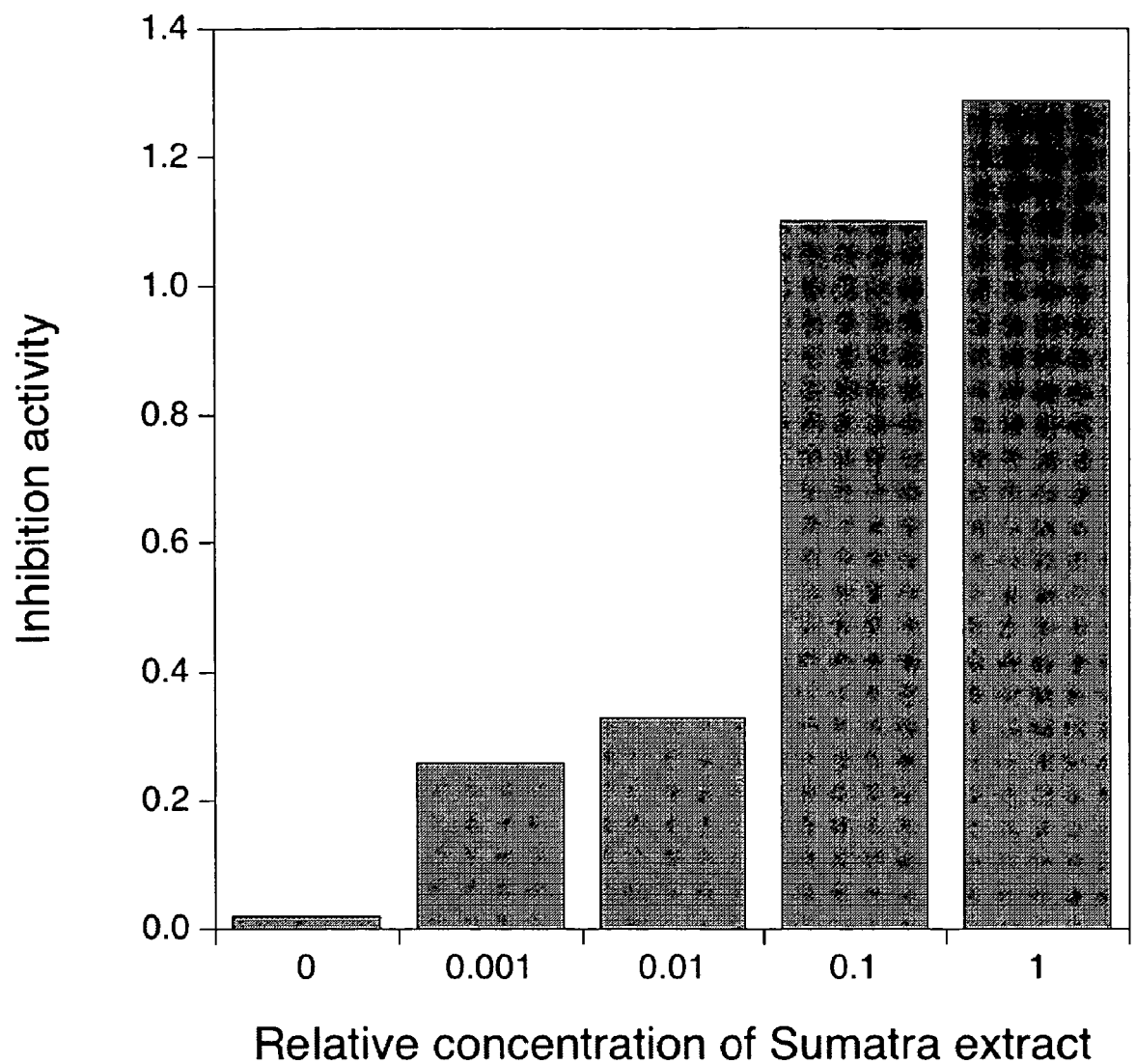
FIG. 3 demonstrates that an ethanol extract prepared from coffee grounds shows a concentration dependent inhibition of PP2A methyl esterase.

FIG. 3 shows the results of an assay using the filter paper method to assay 1 μl of extract per 10 μl of assay mixture. The results show that this ethanol extract of Sumatra coffee grounds shows a concentration-dependent inhibition activity. The inhibitor effect seen is due to a small molecule that is soluble in organic solvents and is not caffeine. The Concentration of pure caffeine required for 50% inhibition of PPME was >440 μM. Inhibitory activity was present at similar levels in both regular and decaffeinated coffee.

Example 5

Assay for Methyltransferase Activity

This example provides guidance for determining activation of PPMT. Purified PP2A AC dimers (see Example 3) are mixed with the purified PPMT (prepared as described in Example 1) and $^3$H-methyl-labeled S-adenosyl methionine and incubated at 37 C. After several minutes aliquots were removed, protein was precipitated with 10% trichloroacetic acid (TCA), washed with 10% TCA, then washed with 100% methanol, and $^3$H-methyl-PP2A was assayed by liquid scintillation counting (Tolstykh, T. et al., *EMBO J.* 19 (21): 5682-91 (2000).

Example 6

Purification of the Component(s) in Coffee that Inhibit PP2A MEase

This example provides methods by which inhibition activity can be measured for a larger number of compounds in parallel in a 96-well plate format, and provides methods through which the inhibitory component(s) in coffee may be selectively enriched or purified.

(a) Inhibitory Effect of Coffee Component(s) on PPME Assayed in a 96-Well Format:

The inhibitory effect of coffee component(s) on PPME was measured using the filter paper method as adapted to a 96-well plate format. Equimolar amounts of PP2A and [$^3$H]-SAM and a two-fold molar excess of PPMT were incubated at 37° C. for 30 min., which is the time when the methylation reaction reaches its equilibrium, and PP2A is close to 100% methylated. Methylated PP2A was separated from PPMT by diluting the reaction mixture in buffer with Ni-NTA resin and bovine serum albumin (BSA) and shaking at room temperature for 30 min. The supernatant containing methylated PP2A was collected, and Ni-resin to which PPMT bound was discarded.

96-well Millipore filter plates were used to assay demethylation of methylated PP2A. Methylated PP2A was mixed with PPME at 37° C. At reaction times of 5 and 10 min, 10 μl of reaction mixture was spotted into a well of the filter plate containing cold 25% TCA to stop the demethylating reaction. The filter in each well was washed with 5% TCA, then with 70% ethyl alcohol, and finally air-dried. Scintillation fluid was added into the wells, and the radioactivity due to bound $^3$H-methyl-PP2A was counted using a Packard TopCount scintillation counter.

(b) Purification of Coffee Components Inhibitory to PPME Using Ethyl Acetate Partitioning.

The inhibition activity in coffee may be purified from extracts of either whole coffee or instant coffee by a selective partitioning into ethyl acetate at low versus high pH.

10 g of ground Sumatra coffee bean (Starbucks) was extracted with ethanol at 80 C for 5 minute with stirring. After cooling, the extract was filtered through a Whatman No. 54 paper filter. The filtered extract was rotary evaporated at 40 C until the volume was reduced to approximately 1 ml. 200 μl of this concentrated extract was mixed with an equal volume of 50 mM MOPS buffer, pH 7.2 with 1 mM EDTA (Buffer A), 0.1M HCl, or 0.1M NaOH, and then extracted with 1 ml of ethyl acetate. After separation by centrifugation, the aqueous and organic phases in each tube were collected, dried under vacuum in a Speedvac concentrator, resuspended in Buffer A to a volume of 2 ml, and the pH adjusted to 7.2. This extract was assayed using the filter paper method with a volume of 1 μl of extract per 10 μl of sample volume. The results of this assay demonstrated an inhibition activity of about 1 (100% inhibition) for the organic phase in the presence of Buffer A or HCl, an inhibition activity of about 0.2 for the organic phase in the presence of NaOH, an inhibition activity of about 0 from the aqueous phase in the presence of Buffer A or HCl, and an inhibition activity of about 1 from the aqueous phase in the presence of NaOH.

1 g of decaffeinated instant coffee also was dissolved in a 10 ml final volume of 0.1M HCl ("acidic coffee solution"). The final pH of the acidic coffee solution was 3.0, and an amount of insoluble material was removed by centrifugation. The amount of insoluble material was larger than the amount of insoluble material present after dissolving 1 g of instant coffee in 10 ml of hot deionized water at pH 5 (the "water-extracted coffee solution"). 5 ml of the acidic coffee solution was extracted with 4 ml of ethyl acetate, and the organic phase recovered. The organic phase then was extracted with an equal volume of 0.1M NaOH. The final extract was clearer and much lighter in color than was instant coffee dissolved in water or HCl. These extracts were assayed using the 96 well plate method and a diluted extract equivalent to a volume of about 0.1 μl of extract per 10 μl of assay mixture. Under these conditions, the water extracted coffee solution had an inhibition activity of about 0.78, the acidic coffee solution had an inhibition activity of 0.44, and the NaOH extract of the organic phase had an inhibition activity of 0.47. These results and the results described above demonstrate that the inhibitory compounds from coffee can be purified by selective partitioning into ethyl acetate at acidic pH and selective partitioning into the aqueous phase at basic pH.

(c) Purification of Coffee Components Inhibitory to PPME Using Ethanol Extraction, Water Wash and Reverse-Phase Separation.

10 g of decaffeinated instant coffee (Taster's Choice) was boiled (80° C.) three times in 100 ml 100% ethanol for 5 min. Each ethanol extract was centrifuged at 3,000 rpm, 4° C. for 30 min, the supernatant collected, and the coffee-solids-containing pellet used for the subsequent extraction. Inhibition activity present in these extracts was measured by the 96 well plate assay described in (a) above.

Figure 4A:
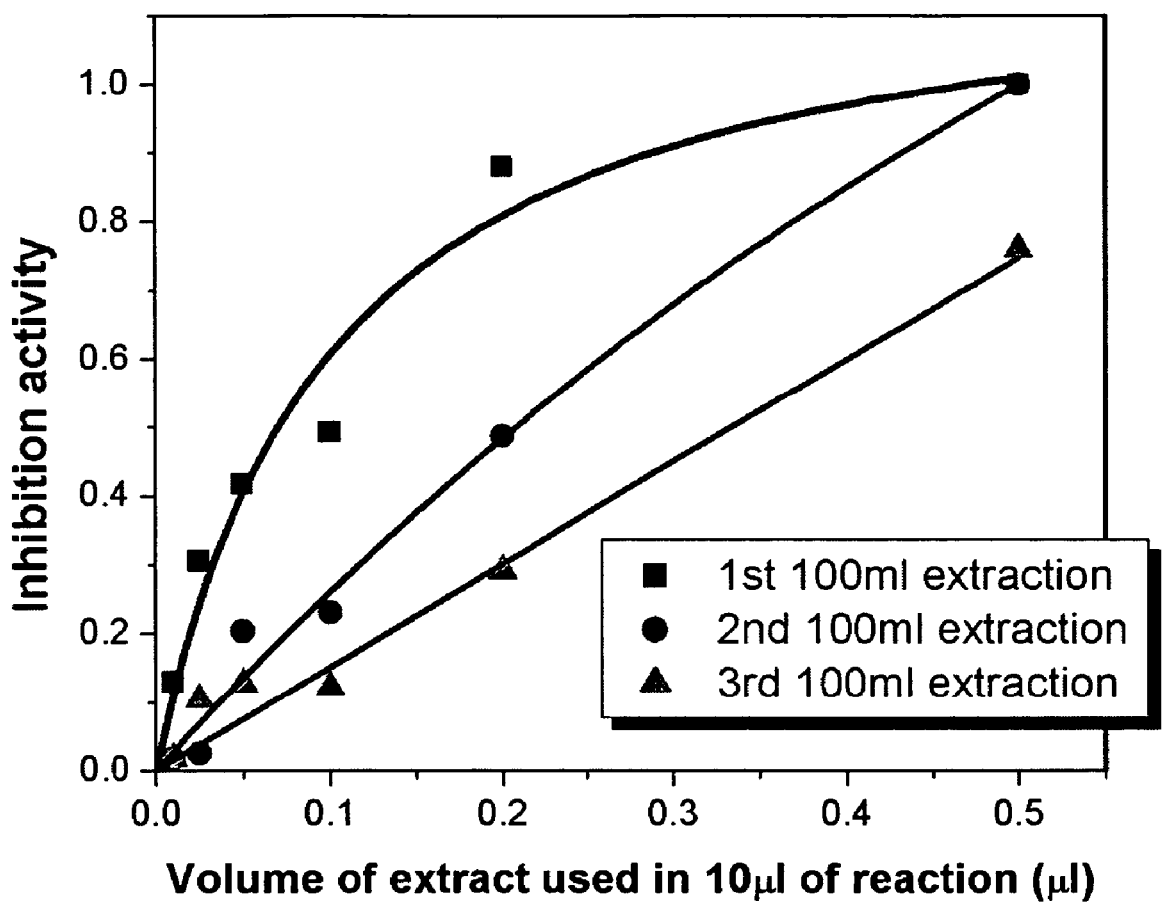
FIG. 4 parts A through D show purification of PP2A methyl esterase inhibitor compound activity extracted from instant coffee by ethanol extraction: (A) PP2A methyl esterase inhibitor compound activity in crude ethanol extract after three 100 ml ethanol extractions, 300 ml total volume; (B) PP2A methyl esterase inhibitor compound activity in crude ethanol extract after two 100 ml and one 50 ml ethanol extractions, 200 ml total volume; (C) PP2A methyl esterase inhibitor compound activity in water wash compared to inhibitor remaining in the water insoluble material. (D) elution profile from a C18 solid phase extraction cartridge showing further purification of PP2A methyl esterase inhibitor compound.

FIG. 4A shows the presence of a methylation modifying compound possessing PP2A methylesterase inhibition activity in an extract prepared from instant coffee by ethanol extraction. FIG. 4A shows PPME inhibition activity in each crude ethanol extract after three 100 ml ethanol extractions, 300 ml total volume. The extracted inhibition activities in the second and third extracts were less than in the first extract, such that activity present in the second and third extractions was about half of the previous extract's activity. Based on this observation, 200 ml EtOH should be enough to extract the majority of the methylation modifying activity in 10 g of instant coffee.

Instant coffee was boiled (80° C.) once in 100 ml ethanol for 5 minutes and twice time in 50 ml ethanol for 5 min each time. Each extract was centrifuged at 3,000 rpm, 4° C. for 30 min, and the supernatants combined to yield a crude extract with an approximate volume of 200 ml. The inhibition activity in the final extract was measured by the 96 well plate assay described above.

Figure 4B:
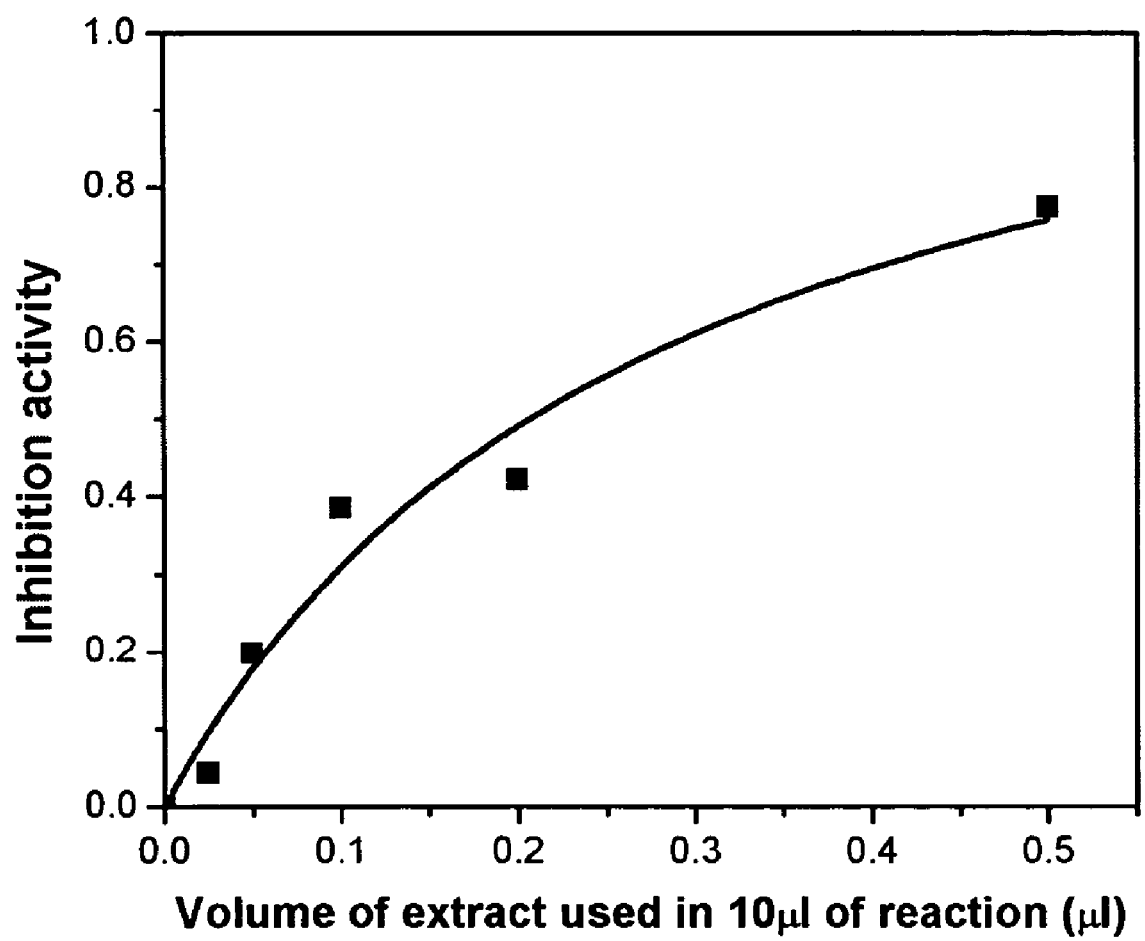

FIG. 4B shows PP2A methyl esterase inhibition activity in crude ethanol extract after these extractions. As shown in FIG. 4B, about $10^6$ units total inhibitory units were extracted in 200 ml EtOH from 10 g coffee.

The ethanol was filtered through Fisher Scientific medium porosity type P5 filter paper (P5 filter paper), rotary-evaporated and the brown, thick residue collected. The residue weighed 1.18 g. The dried coffee residue obtained from the crude ethanol extract was washed four times with 50 ml of doubly deionized water with pH <5. The water solutions were filtered through P5 filter paper. 50 ml of ethanol was used to dissolve components that stuck to the flask, and another 20 ml ethanol was used to wash the filter paper. The material dissolved in ethanol and not dissolvable in water was much lighter in color than was the crude extract.

Figure 4C:
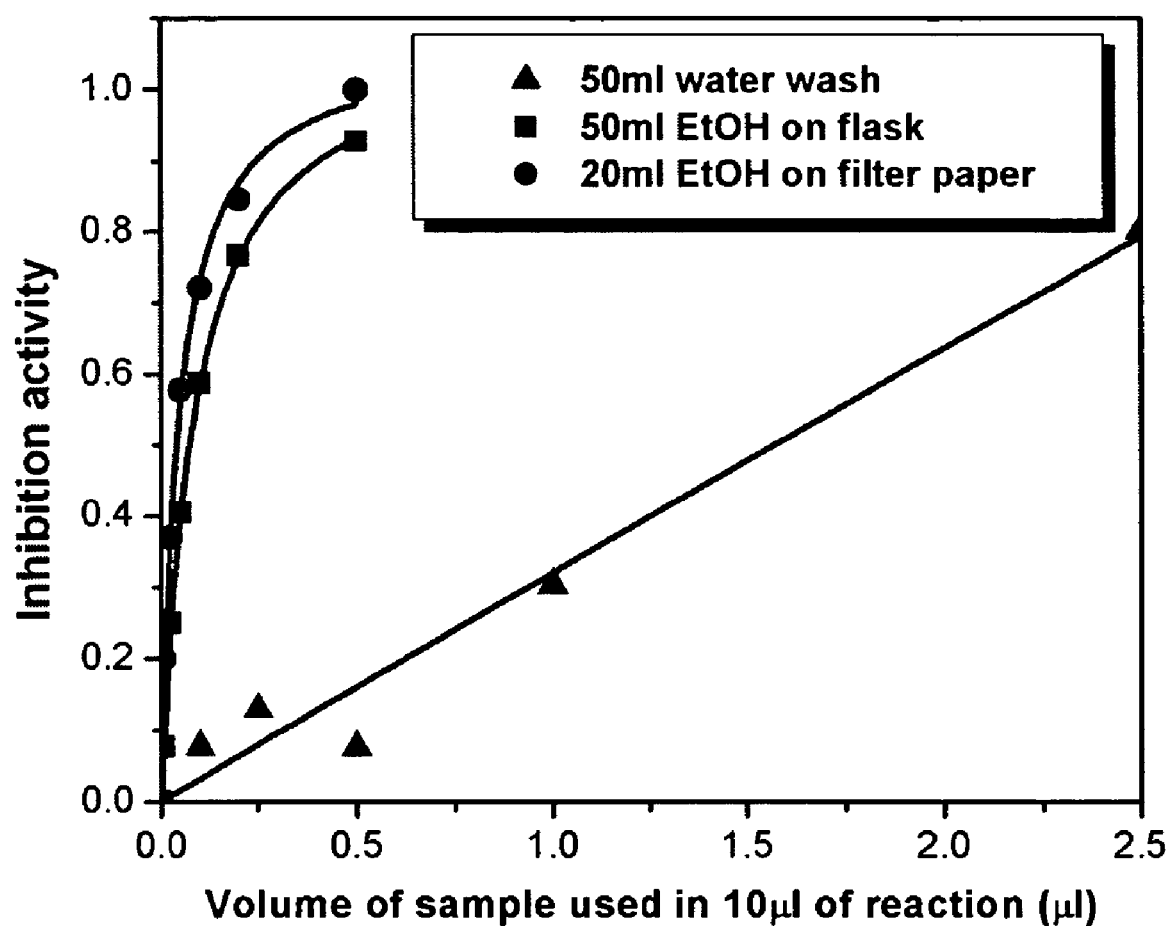

The PP2A demethylation inhibition activity of the water washes, ethanol used to wash the flask, and ethanol used to wash the filter paper are shown in FIG. 4C. Only about 10% of the total inhibition activity in the crude ethanol extract was lost in the water-wash step. The residue dissolved from the flask and filter paper with ethanol was rotary evaporated to yield a final coffee extract containing nearly all the inhibitory activity and having a mass of about 0.1 g.

A solid-phase extraction cartridge containing C-18 resin (Waters) equilibrated with 50% methanol plus 0.1% trifluoroacetic acid (TFA) was used to further purify the inhibitory compound in the final coffee extract. The ethanol in the final coffee extract was rotary-evaporated. The residue was dissolved in 50% methanol plus 0.1% TFA and loaded on the C-18 cartridge. The cartridge then was washed with three column volumes of 50% methanol, 60% methanol, 70% methanol, 80% methanol, 90% methanol, 100% methanol, and 100% acetonitrile, all with 0.1% TFA. Materials eluted with each mobile phase were collected as separate fractions. Water and organic solvents in each fraction were rotary evaporated, and the residue was dissolved in ethanol.

Figure 4D:
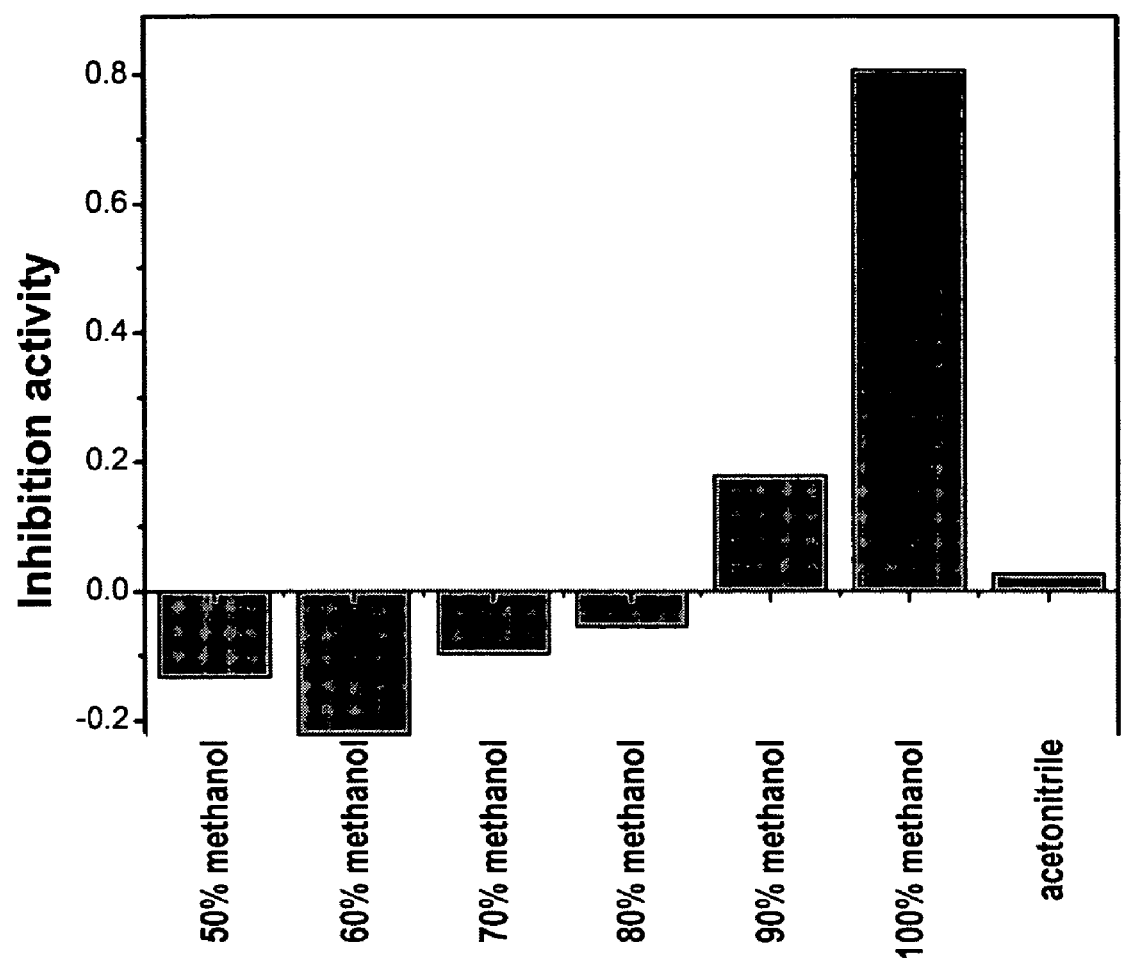

FIG. 4D shows the elution profile of inhibitory activity. Eluent corresponding to 0.5 μl of the final coffee extract was used per 10 μl of PP2A demethylation reaction. The 90% methanol and 100% methanol fractions contained most of the PPME inhibition activity present in the final coffee extract and little or no activity remained to be eluted by the acetonitrile.

Example 7

Identification of PP2A Inhibitory Activity in Botanicals

We have used the assay described above in Example 4 to screen commercially available herbal substances for the presence of a PP2A demethylation inhibitor compound. Each of these substances has been reported to have properties that affect the health and well-being of human subjects. For example, Allicin is an antibiotic and antifungal compound obtained from garlic.

Artichoke powder is believed to have hepatoprotective, antioxidant, and hypocholesterolemic properties.

*Bacopa monniera* is an herb used in India for memory, epilepsy, and as a mild sedative. *Bacopa* commonly grows in marshy areas throughout India. *Bacopa* is believed to have strong antioxidant properties, protect mental function and improve learning skills.

Butcher's broom, an herbal extract that typically contains 10% saponin glycosides as active components, has been reported to have anti-inflammatory properties.

Cocoa powder cocoa contains a high content of phenolic phytochemicals, or flavonoids, indicating the presence of known antioxidants that may protect against cancer, heart disease and other ailments.

Flaxseed oil, which is obtained by extracting the oil from flaxseeds is believed to stimulate the immune system and to have antioxidant, cholesterol and triglyceride lowering and anti-tumor properties.

Grape seed extract contains oligomeric proanthocyanidins (OPCs), a class of flavonoid complexes that act as antioxidants in the body. It is believed that OPCs may help protect against the effects of internal and environmental stresses and may counter the negative effects of high cholesterol on the heart and blood vessels.

Purportedly, nutritional supplementation of inositol may affect behavior and may have anti-depressant and anti-anxiety activities.

St. John's Wort, *Hypericum perforatum*, is an herbal product sold as an over-the-counter treatment for depression. It is being studied for its ability to lessen certain side effects of cancer treatment.

The antioxidants in green tea, black tea and red tea purportedly have significant health benefits, including the ability to prevent cancer and heart disease.

Tobacco extract has been shown to produce a biphasic effect on macrophage respiration: a stimulation at low concentrations and an inhibition at higher concentrations.

The putative health affects of ginseng, gingko, huperzine, Vitamin E (DL-alpha-tocopherol), and choline already have been described above.

Extracts typically were made from the contents of one tablet, capsule or caplet by heating in 1 ml of pure (200 proof) ethanol for 30 minutes at 80° C. before centrifugation for 5 to 10 minutes at 12,000 rpm in a Sorvall MC-12V centrifuge to remove insoluble material. In the table below, this is indicated as a "standard ethanol" extraction. Extracts for tea were made by heating in 10 ml of doubly deionized water at 80° C. for 30 minutes before centrifugation. This is denoted in the table as a "standard water" extraction. Other extractions are as specified, and pure or nearly pure compounds were dissolved in the solvent listed. A portion of each extract was dried to determine the mass of dissolved material in the extract.

TABLE 1

Commercially available herbal substances screened for the presence of a PP2A demethylation inhibitor compound.

| Sample Code | Substance | Extraction method | Source |
|---|---|---|---|
| #3 | Gingko Biloba leaf extract: 60 mg per tablet. 24% flavonol glycosides (14.4 mg), 6% terpene lactones (3.6 mg). Also contains 14 support ingredients. | Standard ethanol | Sundown |
| #4 | Allicin, (garlic bulb extract): 130 mg/capsule. Also contains cellulose. | Standard ethanol | Zhang |
| #5 | Huperzine A, Gotu Kola (Centella asiatica, aerial part) 285 mg, Huperzine 50 µg, lecithin 100 mg/capsule. Also contains 3 support ingredients. | Dissolved in ethanol | Solaray |
| #6 | Bacopa, Himalaya (Bacopa moniera fennel leaf extract): 500 mg/capsule. | Standard ethanol | Brahmi |
| #7 | Butcher's Broom: root extract with other ingredients, no amount was shown on the bottle label. Also it is not clear whether or not support ingredient was included. | Standard ethanol | TWINLAB Nature's Herbs |
| #10 | Flaxseed oil - contains 1425 mg of linolenic acid, 450 mg of oleic acid, 400 mg of linoleic acid, 150 mg of palmitic acid, 75 mg of stearic acid/2 softgels. Other ingredients: flaxseed oil. Oil volume is about 1.4 ml/soft gel. | Dissolved in DMSO | Solgar |
| #12-1 | DL-α-tocopherol,, 95%, MW 431, prepared from synthetic phytol. | Dissolved in ethanol | Sigma (T3251-25G) |
| #21 | Ginseng - 100 mg of Ginseng extract/caplet, 7% ginsenosides in the extract, also contains calcium carbonate et al 16 ingredients | Standard ethanol | Your Life |

TABLE 1-continued

Commercially available herbal substances screened for the presence of a PP2A demethylation inhibitor compound.

| Sample Code | Substance | Extraction method | Source |
|---|---|---|---|
| #22 | Grape Seed Extract, 100 mg of grape seed extract (85% polyphenols)/tablet, also contains calcium carbonate et al 11 ingredients. | Standard ethanol | Wegmans |
| #23 | St. John's Wort, 300 mg of St. John's wort extract (0.3% total dianthrones)/caplet,, also contains cellulose et al 11 ingredients. | Standard ethanol | Wegman's |
| #24 | Artichoke-powder, 100 mg of artichoke (aerial part) extract and 375 mg of artichoke (aerial part)/capsule, also contains vitamin E et al 4 ingredients. | Standard ethanol | Nature's Herbs |
| #25 | Choline & Inositol Capsules, choline 250 mg and inostol 250 mg/capsule, also contains gelatin et al 5 ingredients. | Extracted with room temperature ethanol; otherwise standard. | Twinlab |
| #26 | Green Tea, 1.5 g/bag, ingredients: green tea, verbena, lemongrass, lemon flavor. | Standard water | Wissotzky |
| #27 | Red Bush Tea, 2 g/bag, Ingredients: South African rooibos (Aspalathus linearis) and lemongrass with 15 mg of SGS made from broccoli seed. (no caffeine) | Standard water | Brassica |
| #28 | Black Tea, 2.1 g/bag, Chinese black tea with 15 mg of SGS made from broccoli seed, caffeine | Standard water | Brassica |
| #30E | Tobacco No additive. Sliced tobacco leaves. | 820 mg extracted with 10 ml ethanol for 60 min at 80° C. | Natural American Spirit |
| #31 | Cocoa, unsweetened -. | 150 mg of the powder was extracted using standard ethanol extraction. | Ghiradelli Chocolate Co. |
| CCM | Curcumin | Dissolved in ethanol. | LKT Laboratories, Inc. |
| CGA | Chlorogenic acid ("CGA"), predominantly trans(ex coffee seeds) 99%, MW = 354.3 | Dissolved in 50% ethanol. | Acros Organics |
| DHCA | 3,4-Dihdroxycinnamic acid ("DHCA"), predominantly trans isomer 99+%, MW = 180.6 | Dissolved in 50% ethanol. | Acros Organics |
| HMCA | 4-Hydroxy-3-methoxycinnamic acid ("HMCA"), 99%, MW = 194 | Dissolved in 50% ethanol. | Acros Organics |
| QA | D(−)-Quinic acid ("QA"), 98%, MW192.17, | Dissolved in buffer. | Acros Organics |

The concentration of each substance that resulted in an inhibition activity of 0.5 (50% inhibition of PPME) was determined using the filter paper method described above in Example 4, and is hereafter referred to as the $IC_{50}$. The results, which are expressed as dry extract weight/ml except as noted, are shown in Table 2.

TABLE 2

Effect of Substances on PPME activity (assayed against PPME at 85 nM by the filter paper method.

| Sample Code | Substance name | $IC_{50}$ |
|---|---|---|
| #3 | Gingko (extract) | 106 μg/ml |
| #4 | Allicin (extract) | 100 μg/ml |
| #5-1 | Huperzine | No inhibition at 40 μM |
| #6 | Bacopa (extract) | 63 μg/ml |
| #7 | Butcher's broom | 37 μg/ml |
| #10 | Flaxseed oil | 1.3 mg/ml |
| #12-1 | DL-α-tocopherol | 35 μM |
| #21 | Ginseng (extract) | 360 μg/ml |
| #22 | Grape seed (extract) | 25 μg/ml |
| #23 | St. John's wort (extract) | 22 μg/ml |
| #24 | Artichoke-powder (extract) | 260 μg/ml |
| #25 | Choline & inositol caps (extract) | 75 μg/ml |
| #26 | Green tea (extract) | 179 μg/ml |
| #27 | Red bush tea (extract) | 45 μg/ml |
| #28 | Black tea (extract) | 50 μg/ml |
| #30E | Tobacco (extract) | 344 μg/ml |

TABLE 2-continued

Effect of Substances on PPME activity (assayed against PPME at 85 nM by the filter paper method.

| Sample Code | Substance name | IC$_{50}$ |
|---|---|---|
| #31 | Cocoa, Ghirardelli Chocolate Co., unsweetened | 92 µg/ml |
| CCM-L | Curcumin-(LKT Co.) | 771 µM |
| CGA | Chlorogenic acid | >1 mM |
| DHCA | Dihydroxycinnamic acid | >1 mM |
| HMCA | Hydromethoxycinnamic acid | >1 mM |
| QA | Quinic acid | >10 mM |

For purposes of this table, the unit of concentration in the above table (µg/ml or mg/ml) refers to dried extract weight (DEW) unless otherwise noted. A ">" symbol before the IC$_{50}$ value means that the IC$_{50}$ concentration is higher than the value tested. Most of these IC$_{50}$ values are high compared to the concentration of the AC dimer of PP2A (30-50 nM) in the reaction mixture.

From these results we conclude that all of these compounds except huperzine, chlorogenic acid, dihydroxycinnamic acid, HMCA, and quinic acid contain significant PPME inhibitory activity. Since the measured activity is dependent on the extraction procedure, the assay described can be used to optimize the extraction protocol and to select varieties or sources of these compounds that contain the most concentrated PPME inhibitory activity.

The present invention has been described with reference to the specific embodiments thereof, it should be understood by those skilled in the art that various changes may be made and equivalents may be substituted without departing from the true spirit and scope of the Invention. In addition, many modifications may be made to adapt a particular situation, material, composition of matter, process, process step or steps, to the objective, spirit and scope of the present invention. All such modifications are intended to be within the scope of the following claims.

What is claimed is:

1. A method of treating a disease, condition, or disorder selected from the group consisting of a cardiac disorder; atherosclerosis; a neurodegenerative disorder; a cerebrovascular disorder; a neuropsychiatric disorder; diabetes: and a combination thereof, the method comprising steps of:
   administering to a subject in need thereof an effective amount of a composition comprising a botanical extract prepared from a botanical raw material selected from the group consisting of *coffea*, ginkgo, garlic, bacopa, butcher's broom, flaxseed oil, ginseng, grape seed, St. John's wort, artichoke powder, tea leaf, tobacco, cocoa, and a combination thereof,
   wherein the composition comprising the botanical extract is prepared by a process comprising steps of:
   (a) solubilizing the botanical raw material in a polar solvent below a pH of about 5 to yield a solubilized botanical material;
   (b) partitioning the solubilized botanical material between an aqueous phase and an organic phase corresponding to the polar solvent above a pH of about 10 to yield a partitioned botanical material in the organic phase;
   (c) separating the partitioned botanical material into a plurality of fractions;
   (d) assessing each fraction of the plurality of fractions to identify an activity inhibiting demethylation of a protein phosphatase 2A (PP2A) enzyme in at least one fraction; and
   (e) collecting the at least one fraction containing the activity inhibiting demethylation of the protein phosphatase 2A (PP2A) enzyme or the combination of fractions containing the activity inhibiting demethylation of the protein phosphatase 2A (PP2A) enzymes to constitute the composition,
   wherein the composition is further characterized as having the following properties:
   (1) the botanical extract is essentially free of chlorogenic acid; and
   (2) the botanical extract contains at least 5 units per microliter of the activity inhibiting demethylation of the protein phosphatase 2A (PP2A) enzyme and thereby stimulates methylation of the protein phosphatase 2A (PP2A) enzyme.

2. The method according to claim 1, wherein demethylation of the protein phosphatase 2A (PP2A) enzyme results from activity of a demethylating enzyme, wherein the demethylating enzyme is a protein phosphatase 2A (PP2A) specific protein methylesterase.

3. The method according to claim 1, wherein the effective amount of the composition is from 1 mg to about 10 g.

4. The method according to claim 1, wherein the botanical raw material comprises a fruit of a species of plant genus *Coffea*.

5. The method according to claim 4, wherein the fruit of the plant genus *Coffea* is a coffee bean.

6. The method according to claim 1, wherein the botanical raw material comprises a ground coffee.

7. The method according to claim 1, wherein the botanical raw material comprises an instant coffee.

8. The method according to claim 1, wherein the polar solvent is a lower alcohol.

9. The method according to claim 8, wherein the lower alcohol is ethanol.

10. The method according to claim 1, wherein the polar solvent is ethyl acetate.

11. The method according to claiin 1, wherein the composition is administered orally.

12. The method according to claim 1, wherein the composition is in the form of a powder.

13. The method according to claim 1, wherein the composition is in the form of a tablet.

14. The method according to claim 1, wherein the composition is in the form of a capsule.

15. The method according to claim 1, wherein the composition is in the form of a lozenge.

16. The method according to claim 1, wherein the composition is in the form of a suppository.

17. The method according to claim 1, wherein the composition comprising the botanical extract contains, at least 10 units of inhibitory activity per microliter.

18. The method according to claim 1, wherein the composition comprising the botanical extract is essentially free of at least one substance selected from the group consisting of caffeine and caffeic acid.

19. The method according to claim 1, wherein the disease, condition, or disorder is a cardiac disorder.

20. The method according to claim 1, wherein the disease, condition, or disorder is a neurodegenerative disorder.

21. The method according to claim 20, wherein the neurodegenerative disorder is Alzheimer's disease.

22. The method according to claim 1, wherein the disease, condition, or disorder is a neuropsychiatric disorder.

23. The method according to claim 22, wherein the neuropsychiatric disorder is Parkinson's disease.

24. The method according to claim 22, wherein the neuropsychiatric disorder is bipolar disorder.

25. The method according to claim 1, wherein the disease, condition, or disorder is diabetes.

26. The method according to claim 1, wherein the disease, condition, or disorder is a cerebrovascular disorder.

27. The method according to claim 1, wherein the disease, condition, or disorder is atherosclerosis.

\* \* \* \* \*